United States Patent [19]

Bass

[11] Patent Number: 5,746,762
[45] Date of Patent: May 5, 1998

[54] DEVICE AND METHOD FOR SURGICAL FLAP DISSECTION

[76] Inventor: Lawrence S. Bass, 4 Garden St., Great Neck, N.Y. 11021

[21] Appl. No.: 720,724

[22] Filed: Oct. 2, 1996

Related U.S. Application Data

[60] Provisional application No. 60/020,363, Jun. 24, 1996, and provisional application No. 60/022,640, Jul. 25, 1996.

[51] Int. Cl.⁶ .................................................. A61H 29/00
[52] U.S. Cl. ........................ 606/192; 604/96; 606/195; 128/20
[58] Field of Search ............... 606/1, 191–199; 128/3, 20; 604/96–99, 104, 105

[56] References Cited

U.S. PATENT DOCUMENTS

| | | | |
|---|---|---|---|
| 157,343 | 12/1874 | Molesworth | 606/192 |
| 5,195,507 | 3/1993 | Bilweis | 128/20 |
| 5,197,948 | 3/1993 | Ghodsan | 604/30 |
| 5,308,327 | 5/1994 | Heaven et al. | 604/96 |
| 5,318,586 | 6/1994 | Ereren | 606/192 |
| 5,439,476 | 8/1995 | Frantzides | 606/192 |
| 5,452,732 | 9/1995 | Bircoll | 606/192 X |
| 5,468,248 | 11/1995 | Chin et al. | 606/192 |
| 5,496,345 | 3/1996 | Kietsurakis et al. | 606/192 |
| 5,514,075 | 5/1996 | Moll et al. | 600/202 |
| 5,514,153 | 5/1996 | Bonutti | 606/190 |
| 5,549,625 | 8/1996 | Bircoll | 606/192 |
| 5,607,443 | 3/1997 | Kietsurakis et al. | 606/192 |

*Primary Examiner*—Nancy Mulcare
*Attorney, Agent, or Firm*—Hopgood, Calimafde, Kalil and Judlowe

[57] ABSTRACT

A device and method for creating an initial cavity in biological tissue within a given tissue type or layer and then expanding the initial cavity into a larger predetermined final cavity by using a dissecting propagating device to dissect the tissue along a plane defined by the initial cavity. The device and method may also produce the additional effect of immediate or delayed tissue expansion resulting in the production of additional tissue length to facilitate excision or to facilitate geometric rearrangement, advancement, excision or closure during surgical procedures. The expansion effect may relate to the dissected layer or an adjacent layer included in the tissue above, below or around the dissected cavity. The dissection method includes a tunneling step followed by a dissector device introduction step followed by an inflation, expansion, dissection step. The device and method of the present invention can be used to perform skin undermining in the subcutaneous fat layer for facelifting cosmetic surgery.

6 Claims, 25 Drawing Sheets

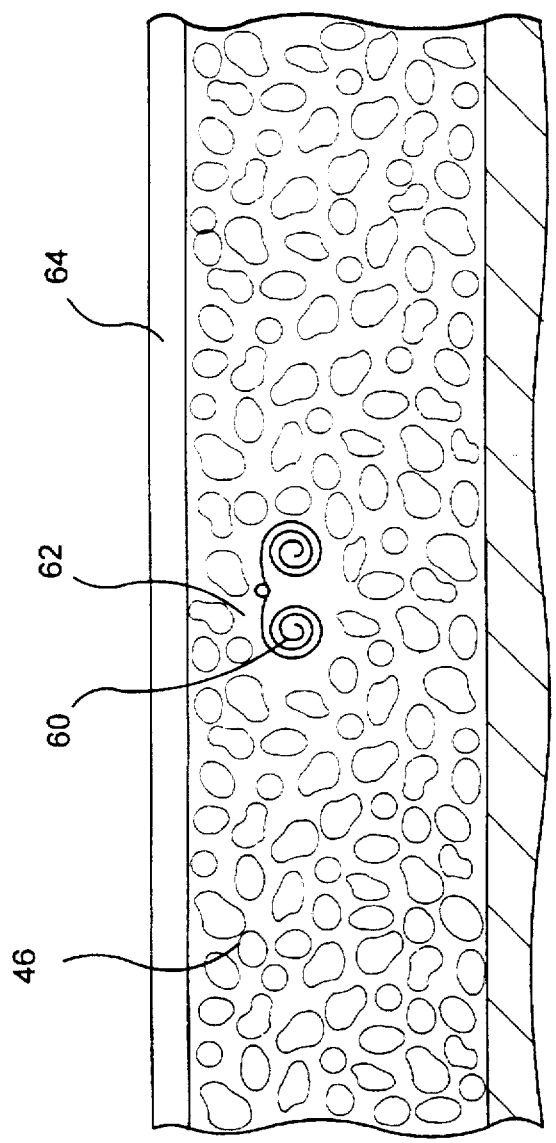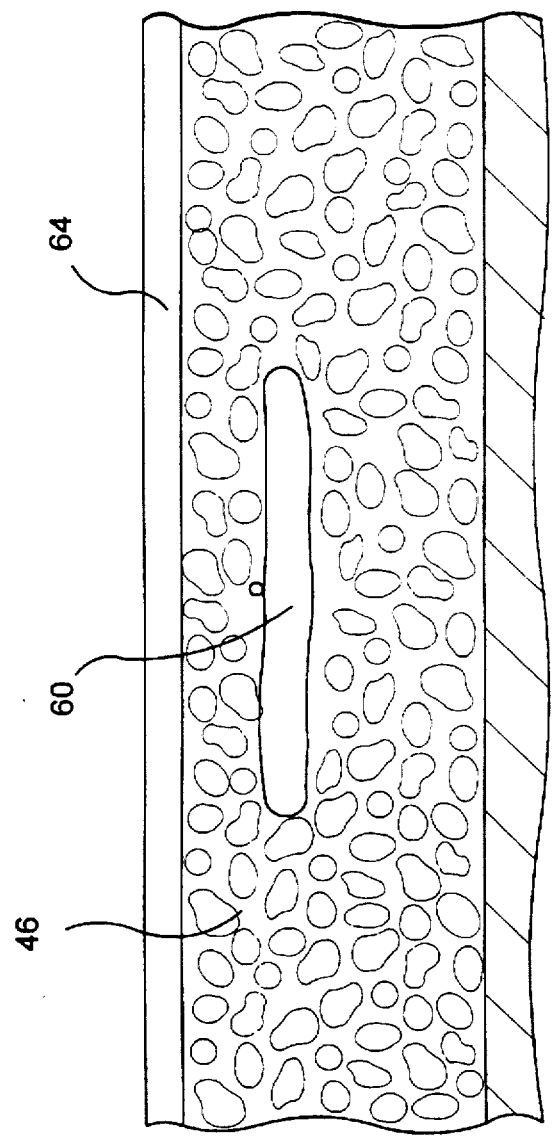

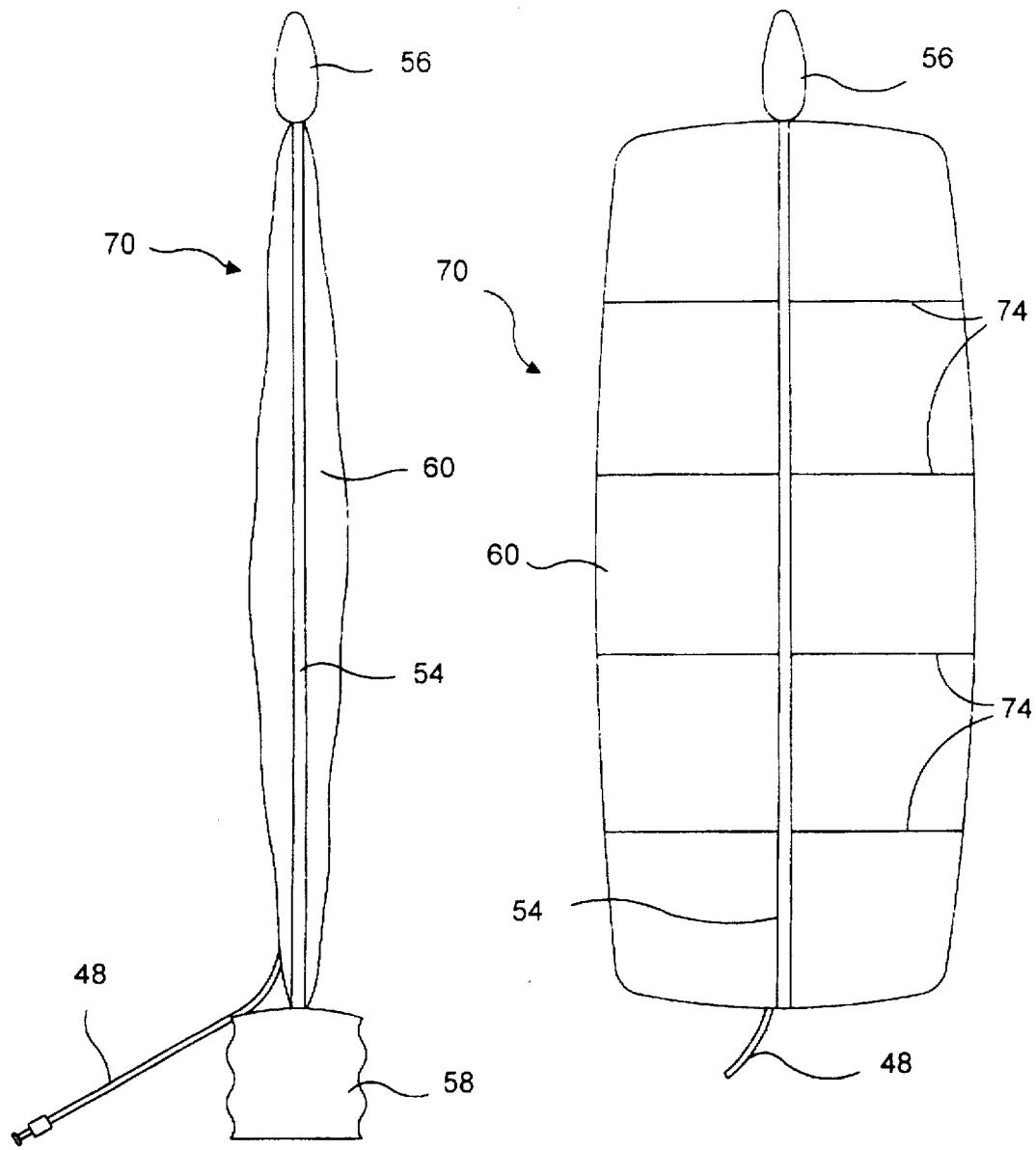
FIG. 6A
FIG. 6C
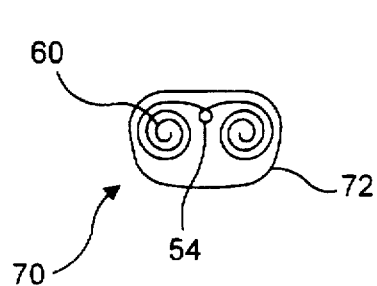
FIG. 6B
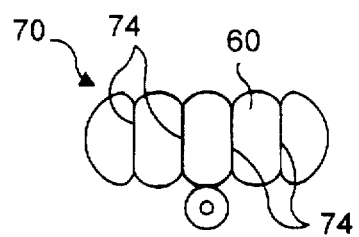
FIG. 6D

DEVICE AND METHOD FOR SURGICAL FLAP DISSECTION

RELATED APPLICATIONS

This application is related to U.S. Provisional patent application Ser. No. 60/020,363, filed Jun. 24, 1996 now abandoned, and U.S. Provisional patent application Ser. No. 60/022,640, filed Jul. 25, 1996, now abandoned, the disclosure of each is herein incorporated by reference.

BACKGROUND OF THE INVENTION

The present invention generally relates to surgical dissection in artificial tissue planes where no natural or potential plane exists, such as, for example, within tissue layers of single tissue types such as muscle, subcutaneous fat, connective tissue or others, more particularly, to tissue dissection within a single tissue type having a segmented pattern that allows dissection along an intended plane of dissection, and most particularly, relates to devices and methods for dissection of adipose fat during facelift surgery.

Skin flap elevation is required in many surgical procedures. In particular, in plastic surgical procedures, skin must often be elevated to translocate it based on a remaining attachment as a skin flap. The flap may used to cover skin defects resulting from trauma or excisional surgery, such as, for example, skin cancers. These plastic surgical procedures can be performed on all parts of the body.

Skin flap elevation must be performed in a precise plane preserving the full thickness of the skin and a certain thickness of underlying fat or the subcutaneous fat. This underlying fat layer contains the subdermal plexus of blood vessels that are responsible for providing an ongoing blood supply to the skin after the skin elevation has been accomplished. Creation of a dissection plane that is too shallow will produce tissue necrosis due to interruption of the blood supply to the skin. A flap including all of the skin plus at least about 1 mm to about 3 mm of subcutaneous fat is preferred. Creation of a too deep plane will remove excessive tissue from the tissue donor site bed and may increase the bulk of the flap being transposed beyond acceptable limits. Additionally, the creation of a too deep plane will increase the risk of injury to underlying nerves, possibly creating facial paralyse postoperatively. A flap including all skin plus no more than from about 3 mm to about 5 mm of subcutaneous fat would be considered borderline and more than about 10 mm of subcutaneous fat would be considered too deep, for most patients. The blood supply to the underlying fat accompanying an excessively thick tissue harvest or elevation may be less reliable than that supplying the skin. If the blood supply is compromised to the underlying fat, necrosis, infection, induration or contour irregularity, among other problems, can result. For these reasons, precise tissue plane or level development is essential for a successful outcome in this type of surgery.

There are other types of tissue flaps or other dissections performed for exposure in surgical procedures that requires separation of tissue in anatomic planes. These are actual or potential tissue spaces that separate one tissue type, anatomic plane or anatomic cavity from another. The degree of adherence of one tissue layer or tissue type to another along actual or potential anatomic planes or anatomic spaces is significantly less than the adherence between tissue layers within an individual tissue type where natural anatomic planes do not exist.

For example, the separation between rectus abdominis muscle and anterior rectus sheath (fascia) is much more easily surgically accomplished than separation of skin from subcutaneous fat. Moreover, creation of a plane at a certain depth within subcutaneous fat, which has no anatomic boundary or separation layer or potential space, is difficult and must be created under direction of a surgeon using a variety of techniques.

Tissue may have a pattern to the structure or organization of the tissue layer. For example, muscle fibers are generally oriented parallel throughout a muscle or a particular component of a muscle. If dissection is initiated between fibers in a given region, dissection can be bluntly extended along the fibers much more readily than across the fibers. Blunt dissection will then tend to propagate along the plane defined by the initial split created in the muscle. This is the essence of a muscle splitting incision.

Fat is organized in lobules that may be split apart bluntly in a similar pattern. Fat is formed in globules rather than long fibers. Consequently, the orientation of propagation of splitting or blunt dissection is more dependent on the formation of an initially defined surgically produced plane and on the direction of application of propagating blunt dissection force.

Surgical techniques for the creation of a non-anatomic dissection or tissue plane can be divided into sharp dissection using cutting tools and energy delivery modalities for dissection. Sharp techniques include knife (scalpel), and scissors. Energy delivery modalities may produce tissue vaporization, ablation, chemical breakdown, thermal breakdown, optical breakdown, sonication, and may employ electrical, sound, light or other electromagnetic radiation of either a monochromatic, polychromatic, coherent or noncoherent type in either continuous or discontinuous fashion.

Blunt techniques are used to separate actual or potential anatomic planes. Such technique may include use of the surgeon's finger, or use of a blunt dissection instrument such as a fork shaped dissecting instrument, blunt obturator, bullet shaped gauze ("peanut" or "sponge-stick"). These techniques have not been regularly used for dissection of surgeon directed planes within a tissue layer, such as, for example, within the subcutaneous fat layer of the body.

More recently, a new class of blunt dissection devices has been developed known as balloon dissection devices. These balloon dissection devices are inflatable devices that are used to dissect a tissue plane or flap of the size and shape of the balloon. These devices have found application in many surgical applications, particularly in the field of minimally invasive surgery where dissection access is limited. (See, for example, U.S. Pat. Nos. 5,496,345 and 5,514,153). Early applications for these devices included endoscopic herniorraphy where the dissector was used to replace blunt instrument dissection in the anatomic plane of the pro-peritoneal space. The devices were similarly used in cystourethropexy in the same anatomic space and employed in dissection of the retroperitoneal tissue plane for aortic, adrenal and lymph node dissection surgery. Access, using these devices, to the subfascial space of the leg for endoscopic vascular procedures have also been accomplished for separating the natural tissue plane between the fascia and the underlying muscle. Plastic surgical applications have included dissection of a pocket for breast augmentation that can be between the pectoralis muscles and the rib cage (subpectoral) or between the glandular breast tissue and the pectoralis muscle (subglandular).

Of the multiple applications in surgery where non-anatomic tissue planes must be created by the surgeon, the facelift operation represents one of the most challenging. In performing a facelift, a large skin flap must be elevated at a level deep to the skin within the subcutaneous fat. This must be done without injuring the overlying skin, such as, for example, by traumatizing the skin with the dissection instrument that could result in necrosis. The tissue plane created by the surgeon must be smooth and even to allow creation of a smooth skin surface after redraping. The tissue plane in the flap must be deep enough to allow adequate preservation of the subdermal capillary vascular plexus that provides blood supply to the skin but cannot be too deep or underlying nerve structures of the face will be injured resulting in facial paralysis post-operatively. Meticulous hemostasis or absence of bleeding must be attained at the conclusion of the procedure, as hematoma is the most common complication of the procedure.

Currently, facelift dissection is most commonly performed with a combination of knife dissection to initiate the correct plane and scissor dissection for completion of the tissue flap. Some surgeons use electrocautery for creation of some or all of this tissue flap.

A great deal of surgical skill and a significant amount of time is required for production of an appropriate facelift flap. Additional time must be spent obtaining meticulous hemostasis after flap creation to prevent postoperative bleeding from all the severed blood vessel connections to the skin. Great care must be exercised to avoid injury to motor branches of the facial nerve to prevent paralysis. Such injury can easily be created by a momentary dip of the scissor tips into deeper layers in the dozens of cuts required to produce the facelift flap. Cautery injury is also a common cause of nerve injury since many small bleeding points across the face are routinely cauterized.

Care also must be taken to create a symmetric flap size and shape on both sides of the face. After flap creation, excess skin is removed. To produce a maximum improvement, the skin and deeper layers must be sutured under some tension. Excess tension is known to create widened scars and risks skin loss. Redraping and fixation (suturing) of the skin must also be performed symmetrically to insure a symmetric result.

As is known, skin has a natural elasticity. Stretching of the skin under direct tension using sutures or inflatable devices can lengthen the skin along a specific axis. This characteristic, called tissue creep, is often used to produce additional skin length to provide enough slack to close wounds where inadequate local tissue exists, as after tumor resection. Skin stretching has also been produced using Foley catheter balloons and tissue expanders. In tissue expansion, an inflatable device is inserted in a tissue plane after dissection using blunt or sharp techniques. The inflatable device is then slowly inflated over many weeks with injection of saline to stretch the overlying skin much the way abdominal skin is slowly expanded during pregnancy. Skin stretching has been performed acutely in the operating room when additional skin length is required to allow wound closure. In this intraoperative tissue expansion technique, the skin is acutely stretched using a tissue expander that is inflated for several minutes before attempted closure. As is known, expanded skin rebounds toward its original length. The degree of rebound varies with the length of the expansion period, the extent of expansion and tissue characteristics.

After facelift, skin removal must be adequate to allow redraping without redundancy or skin overlap. Inadequate skin removal may leave redundant folds of skin. Excessive skin removal increases wound edge tension producing widening of scars during healing and possible skin necrosis.

The traditional subcutaneous plane of skin elevation is widely employed in facelift surgery. Ancillary and alternate procedures have been developed for treatment of aging faces. In particular, in addition to facial skin tightening, dissection in deeper tissue planes has been performed to provide additional tightening, reduce tension on the skin closure and prolong the longevity of the procedure. A layer of tissue underlying subcutaneous fat is the superficial musculoaponeurotic system, hereinafter "SMAS". The SMAS layer is usually dissected or elevated and tightened in facelifting. Alternative approaches to facelifting have employed these deeper tissue planes. Sub-SMAS or subperiosteal dissection and elevation have been employed. Sometimes, these techniques use endoscopic visualization or minimal incisions or both to accomplish the dissection and redraping.

Thus, there is a need for devices and methods for tissue flap creation, such as, for example, facelift flap creation, which require less time and skill to produce the necessary artificial tissue plane to elevate the tissue flap; reduces bleeding during the dissection procedure as compared to sharp dissection; reduces tissue trauma by more widely distributing the forces on the skin was compared to utilization of sharp dissection techniques and high power density energy introduction produced by cautery or laser devices; reduces the time required for performing the surgical procedures; reduces bleeding from the dissection into the tissue plane; produces a softer facelift flap with less swelling and bruising post-operatively; significantly shortens recovery time; reduces skin loss; reduces risk of nerve injury; and provides for the post operative removal of additional skin without increasing the tension of the suture lines due to the intraoperative tissue expansion effect as compared to previous dissection methods and devices.

SUMMARY OF THE INVENTION

The present application is directed to devices and methods for dissection of the non-anatomic tissue planes required for facelifting and other surgical procedures. The surgical dissection for skin redraping in facelift surgery requires creation of a non-anatomic or non-potential plane within rather than between tissue layers, i.e., within a particular type tissue. Surgical dissection, such as, for example, a facelift is performed using inflatable means, such as, for example, balloon dissection techniques for open or minimally invasive procedures to create the tissue flap required for the facelifting procedure. The technique includes introducing an inflatable means such as, a balloon device in the deflated, empty or collapsed state into a space or initial cavity created within a tissue, such as, for example, subcutaneous adipose tissue. The space created is in a nonactual or nonpotential tissue plane often within a specific tissue adipose layer, such as, for example, within subcutaneous tissue or within a muscle. The balloon device is then inflated to enlarge the balloon size thereby exerting pressure on the surrounding tissue. The pressure exerted by the balloon produces tissue dissection in the desired tissue plane. The size, shape and direction of the dissection within the tissue are defined by the size, shape, stiffness, conformation, folding or rolling pattern, unfolding or unrolling pattern, elasticity, expansion pattern and fixation or orientation apparatus of the balloon, among others. The plane of dissection within the tissue is defined by the surgeon based on the plane of insertion of the device and the plane of the cavity produced by the surgeon within the tissue before insertion of the device or during or by insertion of the device, among others.

One basic method of the present application includes a tunneling step in which a small initial cavity or tunnel is created by the surgeon. The initial cavity may be created using blunt or sharp dissection techniques. The initial cavity is shaped to allow insertion of a balloon like expanding/dissecting device in its collapsed, undeployed or deflated state. The position of the initial cavity, tunnel or bore (depth, location) within the tissue, such as, for example, subcutaneous tissue, is an important step that allows the surgeon to define the plane of dissection within the tissue together with the shape, orientation and expansion of the device. A device insertion step in which the dissection/expansion device or the dissection propagating device is inserted into the tunnel or initial cavity created by the surgeon. The device is inserted such that it has the correct orientation and position within the initial cavity for producing the desired plane(s) and/or axis (or axes) of dissection within the tissue. An expansion step, when the device is deployed, activated or expanded to the final shape and size to produce the tissue dissection and/or tissue expansion wanted. This step includes, but is not limited to, release of a lock or stop that had prevented activation, inflation or introduction of an inflating or expanding medium, electrically or mechanically driven expansion and release of a tension producing spring or coil or other means of producing blunt dissection along the plane defined in the tunneling step. The dissection within the tissue resulting therefrom has the final size and shape defined by the dissection expansion device propagated in the artificial plane defined by the surgeon in the tunneling step and the resulting space is hereinafter referred to as the final cavity.

The above-described method provides rapid creation of a precise dissection plane or level within single tissue types between layers or elements thereof, such as, for example, cells, fibers, bundles or fascicles. Utilization of this method during surgery, such as, for example, facelift surgery, will decrease the time required to accomplish the surgical procedure and, thus, reducing the amount of operating room time required for the procedure while reducing complications such as bleeding, tissue damage or necrosis, creation of uneven, irregular or inaccurate dissection planes. The above method also provides for the creation of a precise dissection plane between tissue layers within a single tissue, such as, for example, subcutaneous tissue, where no readily separable plane exists, or where there is no anatomic space or potential anatomic space. The above method also provides for additional intraoperative tissue expansion of the tissue layers above, below or around the dissected cavity. This tissue expansion is simultaneously created with the cavity or at the conclusion of cavity creation by additional inflation of the expansion device. Intraoperative tissue expansion may provide about ten percent (10%) to about fifty percent (50%) increase in length of the expanded tissue.

In one specific method, a surgeon defined a tunnel or initial cavity into which the device will be inserted prior to the device being activated. This initial cavity was produced at the desired level, location, position, plane, orientation and depth required for the surgical procedure. This initial cavity within the tissue defined the level or plane of tissue dissection within the tissue. This defined plane was faithfully propagated by the dissection propagating device to form the final cavity.

In one particularly useful embodiment, the dissection propagating device includes an inflatable bladder or balloon in a collapsed or deflated state after the separate creation of a tunnel or initial cavity as described above or alternatively by precise introduction of the device into a tissue at the level where dissection is wanted, as a means for blunt dissection of a space for the device as described above. Inflation of the balloon was accomplished with the introduction of a gas or fluid to produce a force on the surrounding tissue. The balloon, upon expansion, may accomplish concentric or eccentric expansion to produce sufficient force on the surrounding tissue to cause separation of the tissue thereby propagating the plane produced by the initial cavity to the size of the final cavity within the tissue. Introduction of the gas or fluid produced unrolling or other expansion of the balloon to a size and/or shape in such a manner to apply force in a focal direction to continue dissection along the plane defined by the initial cavity or to produce dissection in a plane defined by the orientation, rotation, or positioning of the balloon. Expansion was continued to provide a cavity of the size and shape required for performance of the procedure, to expose desired anatomic structures, to mobilize tissues for repositioning or for other surgically required ends.

Additional mobilization of tissue can be accomplished by further expanding the tissue without extending cavity size. This mobilization is accomplished because the two individual elements of relatively non-compliant material sealed at the edges, as used in one embodiment of the present invention, will continue to expand out somewhat but will not expand along either long axis or the axis that is in contact with a guiderod but will always expand slightly perpendicular to the axis after full unrolling and/or unfolding. Such expansion of the elements places the tissue under some stretching force but will tend not to allow the final cavity to get any wider or longer but will just elevate the tissue off its bed a little further. Because a much lower force or stretch on the tissue is required to cause continued relaxation of elastic elements of the tissue which takes place slowly over time, merely continuing to place some tension on the tissue significantly below the threshold required for dissection and continuing that tension for a greater period of time will enhance the expansion effect without enlarging the final cavity. Once the final cavity has been formed, it is possible to reduce the expansion media within the elements so that there is a lower pressure, less than the force required to tear apart the cellular attachment within the tissue, on the tissue but still a sufficient pressure on the tissue to accomplish the desired expansion. An addition five minutes of this sort of treatment will produce additional expansion by causing relaxation of elastic elements within the skin without actually tearing any of the remaining subcutaneous fatty attachments. This intraoperative tissue expansion may be produced by stretching the tissues for a brief period or several brief periods separated by rest periods. Tissue expansion is usually performed to the point where tissue perfusion in reduced or stopped during the brief expansion period but without causing permanent cessation of circulation to the tissues or damage to the tissues that would prevent healing. Forces applied vary greatly with the size and shape of the pattern of expansion required and the type of tissue. Pressure on the tissue is often between about one hundred 100 and about five hundred (500) mm of mercury.

One specific embodiment of the device of the present application includes an inflatable component mounted on a rigid or semi-rigid guiderod. The guiderod may be straight or curved in one or more planes. A spheroid tip may be mounted on the end of the guiderod. A handle of adequate size and shape to allow one handed surgeon control of position is attached to or fabricated as an integral part of the end of the guiderod opposite the spheroidal tip.

Another embodiment of the device includes an inflatable component or components that would resemble or be identical to or be a modification of components formulated with the guiderod-tip-handle assembly but without the guiderod-tip-handle assembly.

Objects of the present invention include providing devices and methods for dissection within a single tissue type and for expansion of the resulting skin flap; which stabilizes the position of a balloon to define the position or location of inflation and creation of the dissection and expansion effects in the tissue; to use the tip of the device for creation of the tissue tunnel or initial cavity using blunt dissecting force produced by the surgeon; to utilize the tip of the device to further define or control the dissection/expansion position by transfixing the device either by manual immobilization of the tip once the device is inserted in the tunnel or by advancement of the tip beyond the limits of the tunnel to allow it to be transfixed or immobilized or embedded in tissue distal to the end of the tunnel.

Further objects of the present invention include providing a method for intraoperative tissue expansion simultaneously with flap dissection and for a period thereafter as determined by the surgeon with out using any intervening steps or additional equipment, providing for increased skin removal without increased skin tension, which after rebound, taking place over hours to days produces a tighter skin envelope without excessive skin tension during the initial healing period; reducing risks of wound complications (tissue necrosis, scar widening); and improving the cosmetic result.

Other objectives and advantages of the present application will become apparent from the following description, the accompanying drawings and the appended claims.

BRIEF DESCRIPTION OF THE DRAWINGS

FIG. 4 is a schematic cross-sectional representation of a balloon inserted into an initial cavity in the subcutaneous fat below the skin;

FIG. 5 is a schematic representation of the balloon of FIG. 4 after inflation within the subcutaneous fat tissue;

FIG. 6A is a schematic plan view of a collapsed or undeployed balloon device

FIG. 6B is a schematic cross-sectional view of the device of FIG. 6A;

FIG. 6C is a plan view of the balloon including baffles of FIGS. 6A and 6B in its inflated or expanded shape;

FIG. 6D is a schematic cross-sectional view of the balloon of FIG. 6C.

DETAILED DESCRIPTION OF THE INVENTION

Figure 1C:
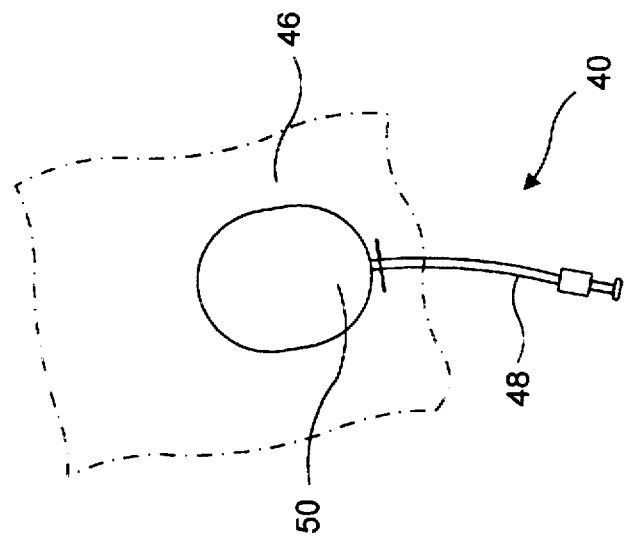
FIG. 1C is a schematic representation of the balloon dissection propagating device of FIGS. 1A and 1B illustrated as being fully inflated in forming the predetermined final cavity.

As is known, in facelifting, incisions are placed in areas that are least visible after healing. Incisions in the check or chin or lip or neck area are avoided. Incisions are placed in hair bearing areas or at the edges of the ear. Pre-auricular and post-auricular incisions are most commonly used which extend into the hair both superiorly and posteriorly. In designing a dissection propagating device, such as, for example, a balloon device to produce the dissection needed for facelifting, anatomic structures, such as, for example, the ear represent barriers to propagation of the dissection. Specific design features of a balloon device are required to allow the necessary dissection without traversing such a barrier. The ear, nose lips and eyes, among others, represent examples of anatomic zones or barriers that cannot be incised or traversed by the balloon.

Nonetheless, in the performance of the facelift surgical procedure, dissection is required in front of and behind the ear as well as below it. Examples of specific features of balloon design incorporated into the present invention for overcoming the above stated problems include the asymmetric shape upon expansion of the balloon and the rolling and/or folding of the balloon in the non-deployed or deflated condition. This rolling or folding may be asymmetric. Rolling may precede folding or folding may precede rolling depending on the direction and sequence of dissection required to avoid intervening barriers or obstacles, such as, for example, the ear, between the insertion site and the dissection site and to provide the required dissection for redraping of the face skin. While these principles of balloon design are directly applicable to facelift surgery, there may also be applicable to other surgery on other areas of the body where anatomic barriers or obstacles must be skirted, asymmetric spaces dissected or where access is limited.

Most of the final cavity or plane within a tissue is produced by dissection using a dissection propagating device. In order for dissection to take place, the surgeon must first gain access to the proper level or plane or position within the tissue by making an initial incision. Once an incision is made, an initial cavity or tunnel is created. This initial cavity, when used together with a particular dissection propagating device, for which the initial cavity was created, is designed to allow propagation of the initial cavity in the desired direction to produce the shape and size required for a predetermined final cavity. The dissection of the tissue for the initial cavity can be produced by sharp dissection instruments including scalpels, knives, scissors, blades, sharp pointed trochars and other sharpened, pointed, slicing, cutting or other similar and like devices. Energy delivery devices such as electrocautery, thermal cautery, diathermy, sonic, laser, light or other electromechanical devices can also be used to perform the initial cavity dissection. Blunt instruments including shafts with oblate, elliptical, spheroid or other similar tips can be used to perform the initial cavity dissection. A forked blunt edged device can also be used.

Using care that the dissection tip of the device, which is the distal end of the device, is positioned at the desired depth within the tissue where the initial cavity is required, the device is inserted by exerting force along the longitudinal axis of the instrument. A handle or grip on the instrument may facilitate manual advancement of the instrument.

Known potential methods or combination of methods that can be used to insure that the instrument dissects at the desired level within the tissue include visual inspection, palpation, imaging with x-rays, ultrasound, magnetic resonance imaging, endoscopic visualization, stereotaxis using mechanical systems or electronic systems having defined fiducial landmarks, or other imaging or positioning techniques in either a continuous or intermittent fashion.

If the dissection propagating device is suitably configured or is contained within or connected to a rigid or semi-rigid tissue introduction system, the device can be used as a blunt dissector device in order to create the initial cavity or tunnel coincident with introduction of the device into the incision. One example is a balloon device that is mounted inside a cannula or over a rigid or semi-rigid guiderod allowing forceful introduction of the device through an initial incision to create the initial cavity. Attachment of a spheroid, oblate, elliptical, olive shaped or other blunt tip to the tissue introduction system would further facilitate the blunt dissection of the initial cavity.

Dimensions of the initial cavity or tunnel are generally significantly smaller than the dimensions of the final cavity. The size of the initial and final cavities along the axis of insertion of the device may or may not be similar or the same. The size of the final cavity along at least one axis will generally be about one and one half (1½) times larger than the dimension of the initial cavity and may be several or many times larger.

Once the initial cavity has been created, the dissection propagating device is inserted into the initial cavity. The expanding or inflating portion of the dissection propagating device is then deployed or inflated, if a balloon, to produce the predetermined dissection along the defined plane according to the characteristics and performance of the particular dissection propagating device. In one particularly useful embodiment of the device, the dissection propagating element of the device is a balloon or bladder. In this embodiment, the balloon is inserted into the initial cavity in a deflated or collapsed state. The balloon may be rolled up for insertion into the initial cavity.

Figure 1B:
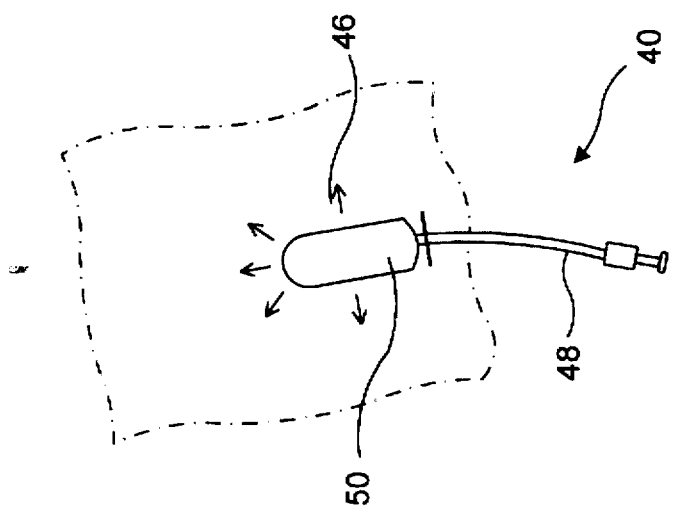
FIG. 1B is a schematic representation of the balloon dissection propagating device of FIG. 1A during the inflation step.
Figure 1A:
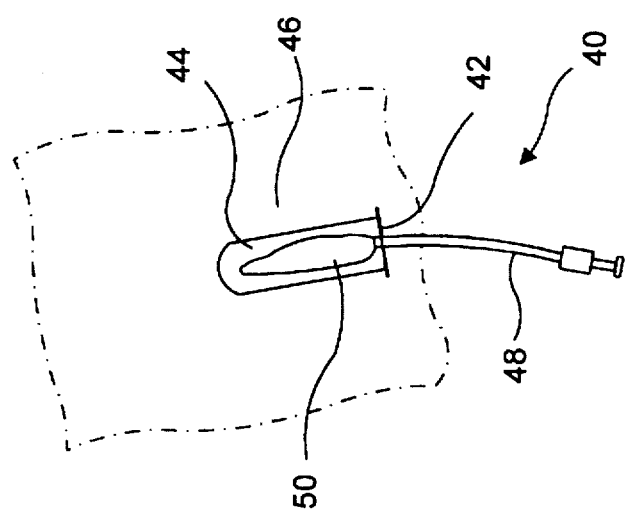
FIG. 1A is a schematic illustration of a basic balloon dissection propagating device positioned inside the initial cavity.

FIGS. 1A-C schematically illustrate a basic balloon dissection propagating device 40 inserted through a skin incision 42 into an initial cavity or tunnel 44 that has already been dissected within the subcutaneous fat tissue 46. The fill port 48 for the balloon 50 is seen exiting from the tissue 46. The balloon 50 portion of the device is shown in the inflated condition thereby creating a sequential enlargement of the balloon 50, as seen in FIG. 1B. The sequential enlargement of the initial cavity can be concentric or equal in all directions or propagated along only one plane or eccentric. Expansion of the balloon portion is continued until the balloon portion is fully inflated to form the desired final cavity, as shown in FIG. 1C.

The balloon dissection propagating device 40 can be inserted into the initial cavity or tunnel in any manner that properly positions the balloon portion for deployment within the tissue. For example, when using a balloon device, the balloon can be slid into the initial cavity or tunnel in a deflated or collapsed state or the balloon can be rolled up in the deflated or collapsed state and then inserted into the initial cavity. Alternatively, the balloon portion can be mounted on a guiderod, as illustrated in FIG. 2, for facilitating insertion and positioning of the balloon portion in the initial cavity.

Figure 2:
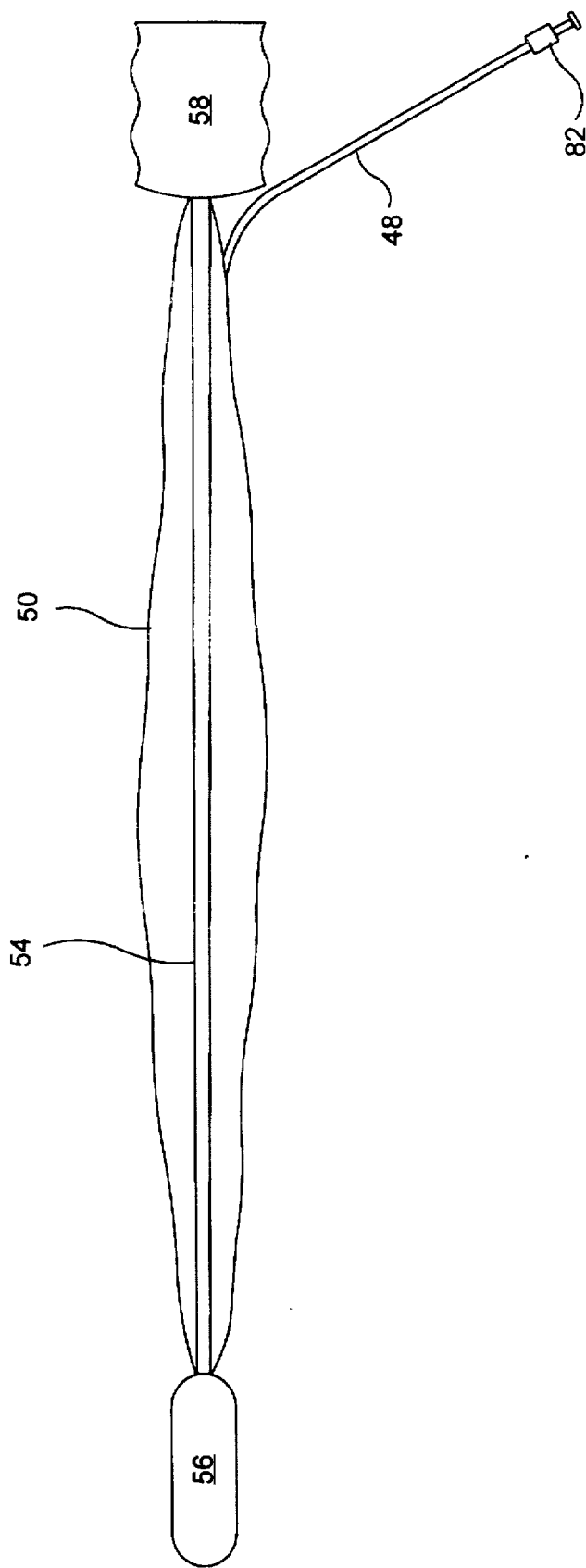
FIG. 2 is a schematic plan view of a representative dissection propagating device including a balloon of the present invention.

FIG. 2 is plan view of a representative dissection propagating device 52, including a balloon 50, of the present invention that may be used with the methods described herein. The guiderod 54 may have a tip 56 for facilitating insertion of the device 52 into the initial cavity without catching the device on surrounding tissue or to provide for blunt dissection to create the initial cavity. A handle 58 may be attached to the guiderod 54 for facilitating ease of use of the device 52 during surgery. The guiderod 54 may be made of metal or plastic or other suitable materials capable of withstanding the force required for introduction of the device into the tissue and during dissection of the tissue without distortion of its shape or disruption of its integrity. The balloon may be permanently or removably attached to the guiderod. The guiderod 54 can by used to stabilize the position of the balloon portion of the device during inflation of the balloon inside the initial cavity.

Figure 3C:
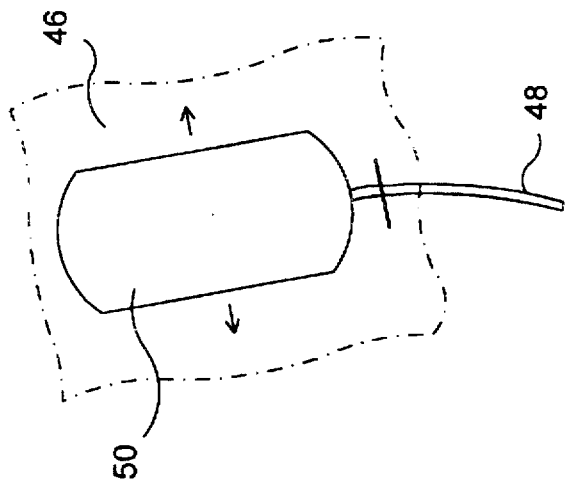
FIG. 3C is a schematic representation of the device of FIGS. 3A and 3B illustrating the balloon portion of the device in its full inflated condition forming the final cavity.
Figure 3B:
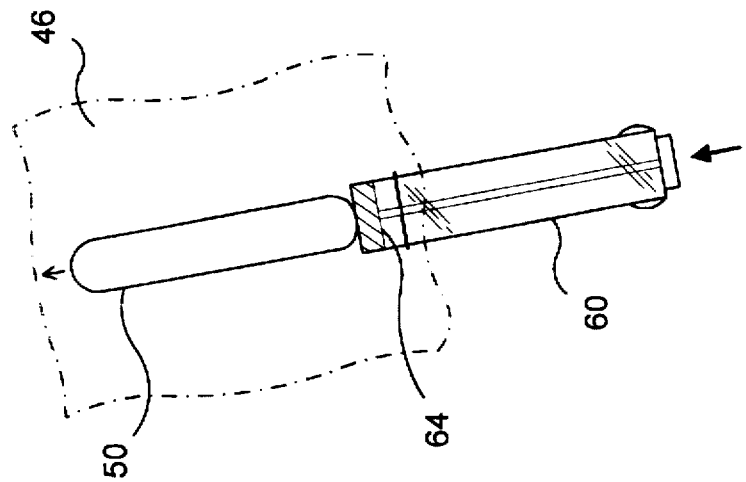
FIG. 3B is a schematic representation of the device of FIG. 3A being advanced out of the introduction apparatus and into the initial cavity.
Figure 3A:
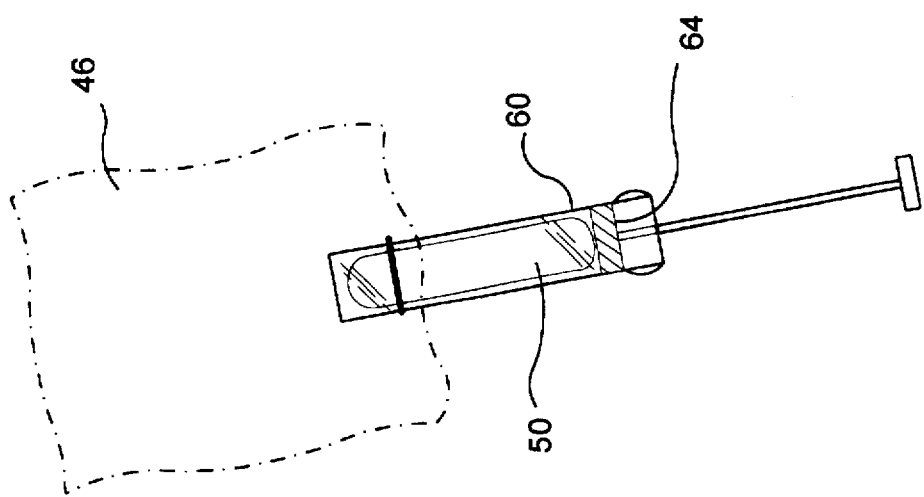
FIG. 3A is a schematic representation of an alternative embodiment of a dissection propagating device including introduction means for positioning the device inside the initial cavity.

Another representative embodiment of a possible dissection propagating device 60 is shown in FIGS. 3A–C and includes placing the balloon inside a cannula, a syringe or other introduction apparatus 62 for positioning the device 60 inside an initial cavity. As shown in FIG. 3B, the balloon 50 is advanced out of the device 60, cannula or syringe, using means 64 such as, for example, a plunger, inflation or by extrusion or other similar means for positioning the balloon in the initial cavity. In one embodiment, the balloon may be integrated with the cannula. With such integration, the cannula can be used for visualization during the inflation of the balloon, for introduction of other instruments into the cavity, for introduction of an endoscope for stabilizing the position of the balloon during inflation or for positioning of the inflated balloon to facilitate retraction during the subsequential procedure after the final cavity has been created. The above last mentioned features are particularly useful for endoscopic procedures or other surgical procedures requiring a minimally invasive approach or through a keyhole incision.

Another method for positioning the balloon within the initial cavity formed within the tissue would be to advance the cannula fully within the initial cavity. Once so positioned, the cannula would be extracted leaving the balloon in position within the initial cavity. Care must be taken to ensure that the balloon is maintained in the proper position within the initial cavity prior to and during the dissection that produces the final cavity.

After insertion or placement of any of the above described dissection propagating devices in the initial cavity, in order to achieve dissection and the formation of a predetermined final cavity, the device must be deployed. In the case of balloons or bladders, deployment is accomplished by inflation. The balloon is inflated thereby increasing its size and producing forces on the surrounding tissue causing further dissection along the plane within the tissue defined by the initial cavity. This inflation is continued until the final cavity shape and size are obtained. Once the required predetermined final cavity has been produced, the balloon can be deflated and removed. Methods for removing the balloon include, but are not limited to, merely sliding the deflated balloon out through the initial incision, wrapping the balloon around the guiderod, etc.

As illustrated in FIG. 4, a cross-sectional view shows a balloon 60 inserted in an initial cavity or tunnel 62 produced in the subcutaneous fat 46 below the skin 64. FIG. 5 shows the same balloon 60 after inflation within the subcutaneous fat tissue. As can be seen, a cavity has been produced which is oriented perpendicular to the initial cavity. As shown, this cavity has been produced within the tissue layer of subcutaneous fat at the level or depth defined by the initial cavity or tunnel. According to the present invention, the position of the level or plane of the final cavity within the tissue was defined by the level or plane of the initial cavity within the tissue. Placement of an initial cavity deeper or more superficial will produce a cavity in a deeper or more superficial position.

It should be understood that the initial cavity and the resulting final cavity could be positioned at a plurality of different depths or planes within the fat tissue layer compared with the overlying skin and underlying muscle in a plane defined by the surgeon during the creation of the initial cavity.

Other factors including the orientation of the force vectors produced by the dissection propagating devices influence the dissection of the final cavity besides initial cavity size and position. However, initial cavity size and position are the principle determining factors. The orientation of the force vectors produced by the inflation of the balloon can be equal in all directions or eccentric taking place to a greater degree in one direction or plane than another. These force vectors will affect the final shape or size of the final cavity, while the initial cavity position or depth will represent the surgeon defined starting point for the final cavity, thus fixing the position or plane within the tissue that the predefined pattern of the balloon or other dissecting device will dissect along to produce the final cavity. Clearly, the direction of cavity propagation is influenced by the orientation of the forces produced by the inflating balloon. Thus, for a given initial cavity, a variety of final cavities can be produced depending upon the dissection characteristics of the dissection propagating device.

As discussed in the background, tissue type plays an important role in the formation of controllable cavity sizes and shapes in a surgically acceptable, atraumatic fashion. As is known, nerve tissue tends to be relatively homogenous in texture with no macroscopically discernable tissue pattern. No readily definable tissue plane is known to exist in central nervous system tissue that does not produce significant functional disruption of the nerve connections within that tissue. The dissection of central nervous tissue would violate one object of the present invention in that a relatively bloodless, atraumatic dissection as compared to conventional dissection techniques would not be accomplished therein.

As is also known, tissue layers consisting of fat tend to have many permissible orientations for the plane of dissection due to the small structural subunits, fat globules and fibrous fenestrations, within this particular type of tissue. Muscle also tends to have a clearly defined orientation of readily dissectable tissue planes due to the uniformity of structural elements within muscle tissue.

Several different strategies can be used to produce dissection in the desired direction or to produce force in the desired direction. In the specific embodiment of balloon dissection propagating devices, force can be produced by unrolling and/or unfolding a balloon or bladder to assume a predetermined shape. The direction of unrolling and/or unfolding produces force vectors in the desired directions as does the size and shape of the balloon and the contour or profile of the balloon height.

FIGS. 6A–D illustrate representative examples of unrolling, during inflation, balloon dissection propagating devices 70. FIG. 6A is a plan view of a collapsed or undeployed unrolling balloon device with FIG. 6B being a cross-sectional view of the device. An optional sheath 72 that may be placed around the balloon for providing easier insertion into the initial cavity and for preventing premature unrolling is shown. This sheath 72 can be manually removed prior to inflation or can be removed or ruptured by the expansion of the balloon. To allow rupture, perforations are placed in the sheath to facilitate sheath opening under pressure during deployment or inflation. The sheath can be designed to allow preferential opening proximally or distally to facilitate initiation of balloon deployment or inflation in a given direction. This controlled deployment and/or inflation and unrolling of the balloon can be produced by a variety of methods. In one representative example, the perforations can be more extensive, larger or deeper on the portion of the sheath where earlier release is needed. In another representative example, the sheath can be made thinner in the area where earlier release is needed. A variety of additional methods of selectively weakening the sheath materials are possible including, but not limited to, varying the degree of polymerization, heat exposure in processing or other methods of decreasing compliance and increasing fragility or brittleness.

As shown, the balloon or bladder can be rolled up in one direction when in the deflated or collapsed state to provide unrolling in a predetermined direction upon inflation thereof. Folding or imbrication of the balloon can also be performed prior to insertion or application of the outer sheath. This can allow further variation in the expansion pattern of the balloon. For example, telescoping of the balloon is possible to allow focused expansion along a given plane. Folding or imbrication can also produce sequencing of expansion of various regions of the balloon. Finally, folding the balloon in an accordion-like manner is also believed to be effective for tissue dissection.

FIGS. 6C and D illustrate plan and cross-sectional views respectively of the balloon device in its inflated or expanded shape.

Where balloons or bladders are used to perform propagation of the dissection produced in the initial cavity, the balloons can be inflated with a variety of media to produce the desired force required for dissection, including but not limited to gases, such as, for example, air, oxygen, carbon dioxide, nitrous oxide, and nitrogen, among others. Gas, being compressible, will tend to produce the greatest expansion in the balloon along dimensions where the least resistance from the tissue or from the balloon or both is encountered. This means that dissection can be directed based on the attributes of the tissue if the tissue tends to allow propagation of dissection along the desired direction. The balloon can be constructed such that the direction of dissection takes this attribute of gas into account when planning the final cavity.

Liquids can also be used for inflation or expansion of a balloon. Possible liquids include water, saline, normal saline, lactated Ringer's solution, or mineral oil, among others. Liquids, being non-compressible, are an expansion medium that provides less compliance than gas, for example. This relative non-compressible feature facilitates production of forces along the vectors of intended dissection to form the final cavity.

Many attributes of the balloon also affect the behavior of the dissection. The balloon can be constructed of a monolayer, bilayer or multiple layers. Each layer may serve similar or different purposes. Possible layer functions include, but are not limited to, water tightness, strength, expansibility, limitation of expansion, and optical lucency. The balloon may also have internal or external elements or members 74 (see FIGS. 6C or D). These include, but are not limited to, ribs, baffles, channels or internally integrated or externally mounted guiderods, cannulas, channels, instrument ports, fiberoptic cables, or others.

Pressure transducers, pressure sensing channels or like modifications are specific possible components of a balloon dissection propagating device as described herein. These components may be used to measure internal balloon pressure, external pressure or dissection force or both external pressure and dissection forces. Additional elements may be direct to controlling the final shape of the balloon, reinforcing its strength, facilitating or controlling inflation sequence or other inflation characteristics.

It is important to the practice of the methods described herein that the size and shape of the final cavity be precisely controlled. Thus, the inflated size and shape as well as the sequence of deployment and/or inflation of the balloon must be carefully controlled.

Wall thickness may vary from region to region within the balloon in a continuous or discontinuous fashion. Variations in thickness affect wall strength, sequence of inflation, degree of expansion, degree of dissection force created and direction of dissection force vectors. These factors may be varied to produce the characteristics required for a given application.

Balloons usable with the devices of the present invention are generally capable of producing between about one hundred (100) and about five hundred (500) mm of mercury force, although this should not be considered a limiting condition, as specific force requirements will vary with the size and shape of the cavity, tissue type and area on the body.

Possible materials for balloon construction include, but are not limited, to plastics, polymers, fabrics, cloths, composites or metals, among others. Specific material for the valve and structural methods for the wall and structural members of the balloon could include Mylar, polytetrafluoroethylene, silicone elastomer, polyethylene, nylon, polyvinyl chloride, latex, Dacron, and polyester, among others. Non-compliant wall materials will tend to produce dissection to a fixed desired shape or in a fixed direction. This is facilitated by assembly of the balloon in a rolled state prior to deployment and inflation. Use of expandable materials in the balloon wall or structural members tends to produce expansion to the force of the compressible material if a gas or other compressible material is used in expansion, or along the vector in tissue where least resistance is encountered. This path of least resistance may be caused by the natural structural characteristics of the tissue or by the attributes of the initial cavity created by the surgeon or both or it may be the result of other factors.

Pressure inside the balloon or on the surface of the balloon can be monitored via an external or internal pressure transducer (not shown) to find out the desired maximum pressure of inflation of the balloon, to control the dissection of the final cavity or the limits of intraoperative tissue expansion. Intraoperative tissue expansion can be performed using a fixed regimen of time or pressure or time and tissue blanching or other endpoint. This can be performed repeatedly with fixed intervals between expansion to the desired degree of tissue expansion or to another endpoint. Tissue perfusion monitoring or other means may be used to determine the extent, endpoint or safety limits of the expansion.

Dissection propagating devices of the present invention, include balloons or bladders that expand or inflate or enlarge or apply force concentrically, eccentrically, or in a complex fashion three dimensionally. Any technique, combination of techniques or degree of use of techniques is possible to produce the desired complex three-dimensional forces required to accomplish the dissection of the tissue to the desired shape and size of the final cavity and the required force to match different tissue types and locations on the body. Further, matching of desired dissection effects and tissue expansion criteria may require further modification to the mixture of techniques and/or methods used to produce the required effects that are likely to be different from that required for dissection or tissue expansion alone.

Multiple dissection propagating devices having balloons may be required to produce the desired final cavity. Each device would be used to produce a certain predefined portion of the final cavity. These devices could be placed in a nested fashion or in different axes or directions within one or more initial cavities. The devices could be placed simultaneously or sequentially. The devices could be inflated sequentially or inflated simultaneously. Multiple permutations and combinations of the above are possible, as long as the result is the creation of the desired final cavity, depending on the surgical requirements and the characteristics of the tissue based on type and location on the body.

Dissection propagating devices could include devices that assume a desired expanded shape and are collapsible to a suitable shape for insertion, the act of collapsing the device could include simultaneously loading a spring or coil along an axis of the required force production. Release of the spring or coil would apply force to expand the device to its original shape or size to produce the desired dissection.

The methods described above are believed usable with any device that is capable of propagating a surgically defined tissue plane or level with the required accuracy and without deviation from the defined level.

Figure 7:
FIG. 7 is a schematic representation of the area of the face and neck commonly requiring undermining in a plane within the subcutaneous tissue during the performance of a facelift operation.
Figure 8:
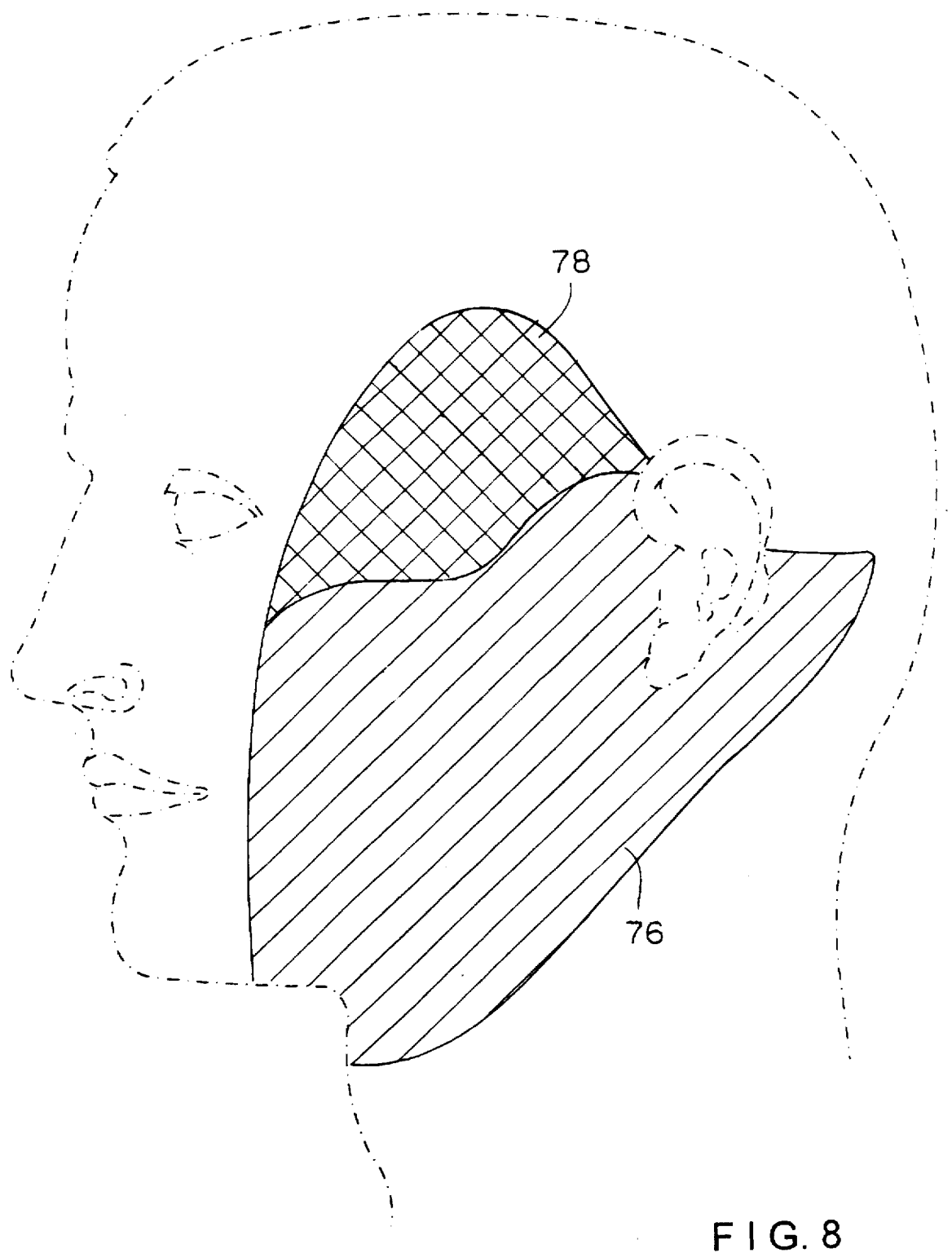
FIG. 8 is a side view of the area of FIG. 7.

In one preferred embodiment of the invention for use in facelift plastic surgery, a device including a balloon component with the shape and size required to dissect a final cavity in a tissue plane required for the procedure can be used. While the precise extent of dissection varies with the individual surgeon and patient, a general area of the face and neck commonly requires undermining in a plane within the subcutaneous tissue as illustrated in FIGS. 7 and 8. FIG. 7 shows an oblique view of the face with a shaded area illustrating the commonly undermined zone of the skin in the facelifting. FIG. 8 is a lateral view of the face illustrating the area commonly undermined in a plane formed in the subcutaneous tissue by single line shading. A second, cross-hatched area represents an additional area of dissection that can be undermined in a plane in the subcutaneous tissue or at a subfascial plane, at the preference of the surgeon.

Figure 9:
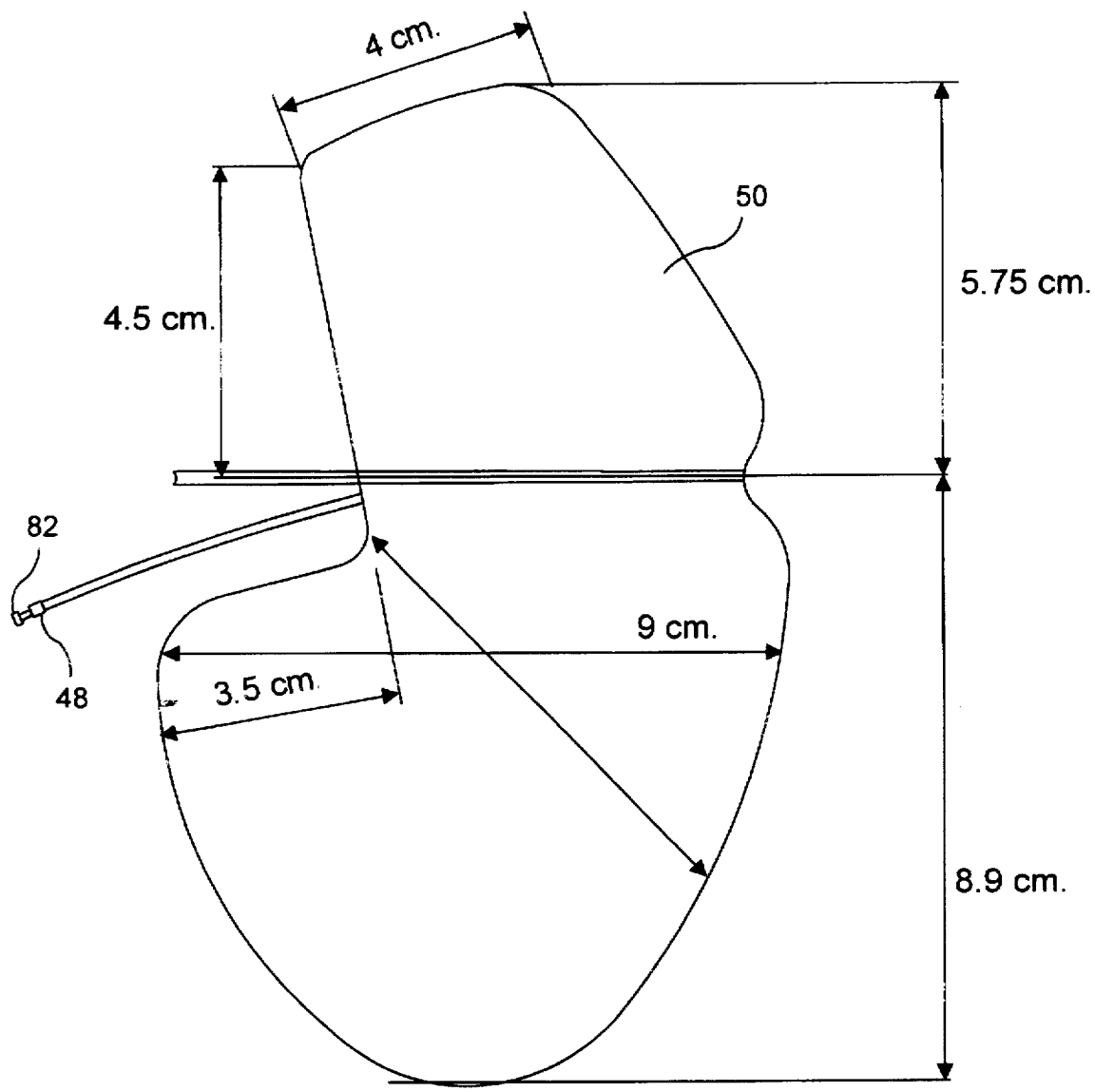
FIG. 9 is a plan view of one representative embodiment of an inflated balloon shape for use in forming the final cavity for a facelift operation.

An example of one representative embodiment of an inflated balloon 50 shaped for use in forming the final cavity for facelifting is illustrated in FIG. 9 and includes approximate dimensions for such a balloon design. Actual dimensions of a balloon for use in a facelifting procedure might be as much as three (3) cm smaller or larger. Several sizes of the balloon may be required to accommodate differences in facial size and shape within the patient population. The balloon material may be made of material described above. The balloon envelope may or may not be expansible or elastic.

In one preferred embodiment of the present invention, a predefined final cavity shape is produced by a balloon with a flexible, non-elastic or minimally elastic wall to obtain the desired dimensions of the tissue dissection while preventing the balloon for merely dissecting along the path of least resistance within the tissue. In forming the balloon or sealing the components, a fill tube 48 is incorporated at some site on the balloon generally closest to the part of the balloon that will be inserted into the tissue most shallowly. This fill tube 48 may be a hollow plastic or metal or composite cylindrical structure that can be attached to a pump or syringe for filling the balloon with an inflation medium. Additional components that may be incorporated in the fill tube include a pressure meter, a fill valve or a release valve or both.

The balloon component may be used alone or mounted onto a guiderod 54 for insertion. In the preferred embodiment of the invention, the balloon is mounted on a guiderod 54 made of rigid or semi-rigid metal or plastic (see FIG. 2). The guiderod 54 may be curved or straight depending on insertion requirements. The tip of the guiderod 54 may be made of a metal or plastic or other material in the shape of a sphere, ovoid, hemisphere or other oblate or blunt shape and of a size larger than the guiderod 54 to allow easy introduction of the guiderod 54 and the balloon by pushing the tissues out of the way. The other end of the guiderod 54 may have an additional piece of metal or plastic or other rigid material mounted on it to form a handle to allow the balloon-guiderod 54 assembly to be inserted and directed easily by the surgeon using one hand. The balloon may be mounted on the guiderod 54 by a plastic or other umbilical of material. The guiderod 54 may be a hollow cannula that is rigid which serves the dual purpose of allowing introduction of the inflation medium into the lumen of the balloon. A rigid cannula into which the balloon may be incorporated or on which the balloon may be mounted to be inflated through the cannula or by separate means may be used in place of a rigid guiderod 54.

The balloon may be folded or rolled or both in any order as required to allow sequential development of various components of the final shape of the balloon according to the shape of the final cavity.

In one preferred embodiment of the invention, an inflatable balloon portion is mounted on a guiderod 54 having a blunt ellipsoid tip at one end and a handle at the other end. The balloon has a hollow flexible cannula or tube connected thereto, the tube opening into the lumen of the balloon at one end and is adapted at the other end for allowing syringe or pump introduction of the inflation medium. The balloon component has preferably two inflatable asymmetric wings that extend laterally from the axis of the guiderod 54. In fabrication of the balloon, the portions of the balloon that extend closer to the handle along the axis of the guiderod 54 than the intended insertion zone is first folded into the lumen of the portion of the balloon that is closer to the tip and will be inserted through the access incision. This provides for introduction of the entire balloon into the initial cavity or tunnel and also allows sequential dissection of first the first portion that is along the length of the initial cavity followed by the second portion that was folded into the first portion that then dissects behind the insertion point. The balloon is then rolled from its lateral edges toward the central portion. This provides for a balloon having a compact shape prior to deployment and/or inflation. The balloon wings can be rolled in the same direction or in opposite directions, depending on the requirements of the dissection. In the preferred embodiment, the balloon wings are initially positioned such that when deployed, they unroll against the superficial surface composed of subcutaneous adipose tissue and overlaying skin outward from the guiderod 54. The balloon can also be initially positioned such that when deployed, the wings unroll against the deep surface composed of subcutaneous adipose tissue and underlaying SMAS outward from the guiderod 54 providing comparable dissection. However, it is presently preferred that the balloon be deployed such that the wings unroll against the superficial surface composed of subcutaneous adipose tissue and overlaying skin outward from the guiderod 54.

Alternatively, the guiderod 54 could be wide enough to insert without tethering on tissue, the guiderod 54 having been fabricated with a blunt end and having grooves formed in the sides of the guiderod 54 for receiving the wings of the balloon in the folded and/or rolled condition.

As shown in FIG. 2, a representative balloon dissection propagating device 80 of the present invention is shown in its non-deployed or collapsed state and includes a handle 58 preferably made of metal, plastic or composite or other rigid, firm, non-bendable material. The handle 58 is adapted to provide for easy grip by the surgeon's hand, allowing positioning of the device and the transmission of force to the guiderod 54 during insertion. The device further includes a guiderod 54 preferably made of metal or plastic and may be curved or straight or bendable but which is sufficiently stiff to withstand the forces of insertion in a preformed initial cavity or insertion with blunt dissection to create an initial cavity. The guiderod 54 is considerably narrower than the balloon portion or the tip 56. The tip 56 is preferably designed to be approximately the width of the collapsed, rolled balloon in order to provide easy insertion of the devices into the tissue without catching on the tissue. The tip 56 can be shaped in a variety of blunt or oblate shapes. The tip 56 also provides stability during balloon inflation by being positioned such that it is firmly inserted into tissue beyond the boundary of the initial cavity or tunnel. The balloon 40 shown in a collapsed or non-deployed state may be rolled or folded or both. The balloon 40 may include contact baffles 74 (see FIG. 6C and D) or sheets of balloon material between the top and bottom walls or sides or other components for regulating the final shape or filling pattern of the balloon in order to form the final cavity.

In one preferred embodiment, baffles 74 between the superficial and deep surfaces of the balloon are present to prevent excessive expansion along the superficial to deep axis. These baffles 74 prevent overexpansion of the overlying skin and possible tearing or laceration of deep structures. The balloon may be covered by an additional sheath to prevent premature unrolling of the balloon. This sheath may be made of a similar material to the balloon or a different material and may be made of soft flexible plastic or it may be a thick protective sheath. The sheath may be removed by sliding back along the long axis of the device toward the handle 58 such that inflation of the balloon if possible or by tearing away from the balloon either manually by the surgeon or during inflation. A hollow tube is connected at one end to the lumen of the balloon and at the other end is adapted to allow injection of fluid or gas by syringe, pump, or other suitable inflation system.

A one-way valve 82 may be affixed to this external end of the fill tube 48 to allow inflation without drainage of the fluid. An additional limb of the tube may allow a drainage valve or a pressure meter. The tube may enter the balloon and travel the length of the balloon with a single opening at the internal end to allow inflation from the distal portion of the balloon to the proximal portion or may have multiple fenestrations along the length of the balloon or may enter the proximal portion of the balloon and not extend any significant distance within the balloon.

Figure 10C:
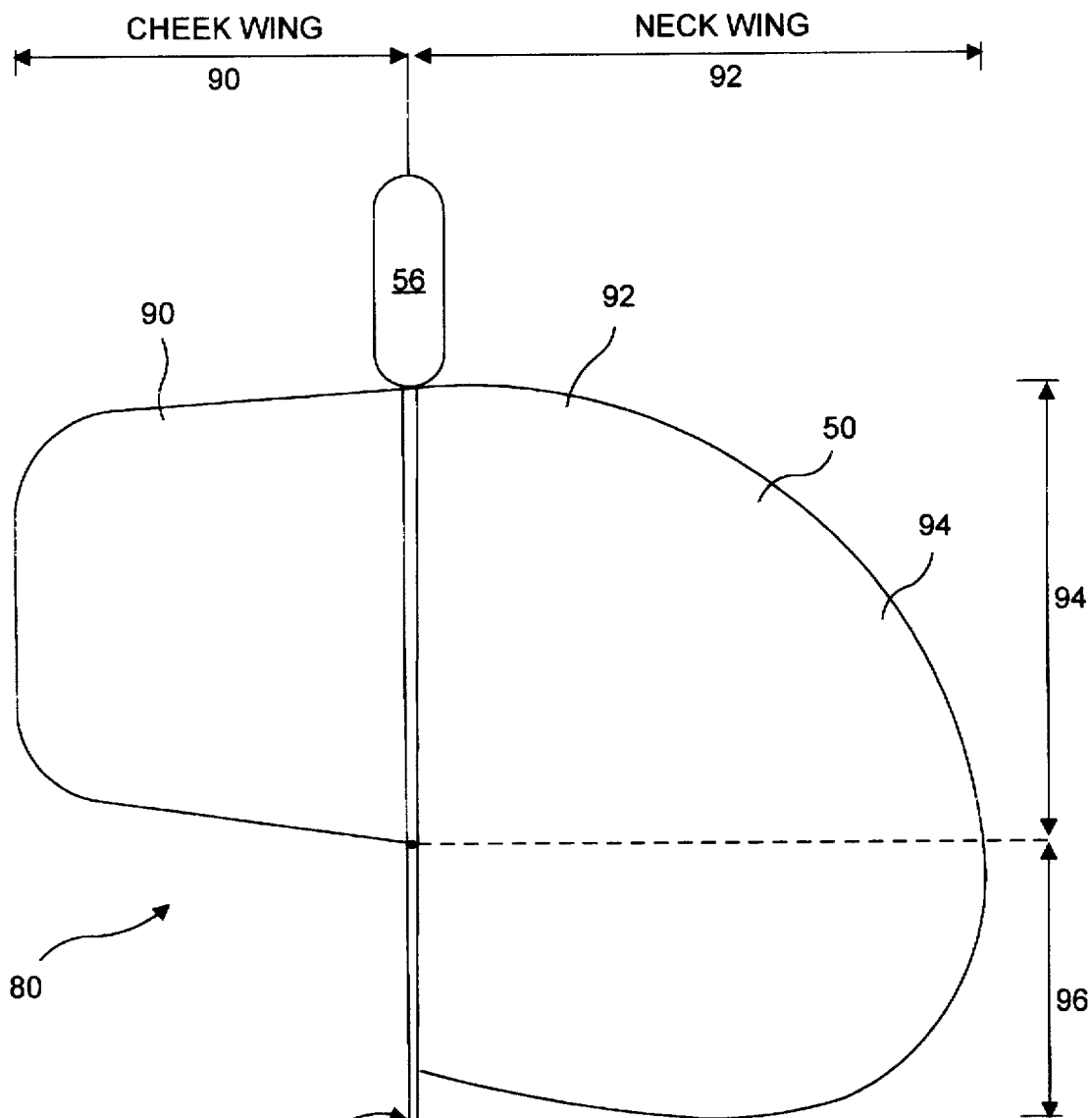
FIG. 10C is a schematic plan view of the preferred embodiment of the facelift dissection propagating device of the present invention in the inflated or deployed condition.
Figures 10A, 10B:
FIG. 10A is a schematic cross-sectional view of a collapsed balloon device including a sheath for preventing premature unrolling or deployment.
FIG. 10B is a schematic view illustrating a balloon in an alternative initial position that provides for balloon deployment by unrolling against the opposite surface from the balloon as depicted in FIG. 11A.

FIG. 10A is a cross-sectional view of the collapsed or non-deployed balloon device 80 including a sheath 72 for preventing premature unrolling or deployment of the balloon 50 during handling or insertion into the initial cavity. Perforations are optionally placed along the length of the sheath 72 to facilitate the controlled rupture of the sheath during inflation. FIG. 10B illustrates a balloon 50 in an alternative initial position that provides for balloon deployment by unrolling against the opposite surface from the balloon as that depicted in FIG. 10A.

FIG. 10C is a semi-schematic plan view of the preferred embodiment of the facelift dissection propagating device 80 of the present invention in the inflated or deployed condition. The balloon device 80, as shown, has two asymmetric wings 90 and 92. The wings are asymmetric in size with regard to the dimension of the balloon along the axis of the guiderod 54 and with regard to the dimension of the balloon that is perpendicular to the axis of the guiderod 54 but within the plane of the representation. Wing 90 represents the portion of the balloon that is adapted to dissect the preauricular or cheek portion of the required facelift dissection. Wing 92 represents the portion of the balloon device that is adapted to dissect the mandibular, neck and retroauricular portion of the facelift dissection. Wing 92 is further divided into two subcomponents, 94 and 96. Subcomponent 94 is that portion of the balloon that is designed to dissect the retroauricular portion of the facelift dissection. Subcomponent 96 is that portion of the balloon that is designed to dissect the mandibular and submandibular or neck portion of the facelift dissection. The position of subcomponent 94 in the inflated state is proximal along the guiderod 54 toward the handle 58 compared to Subcomponent 94. The device 80 is normally inserted through an access incision into the initial cavity or tunnel toward aiming point 108 illustrated in FIG. 12C. Such positioning would mean that when subcomponent 96 is inflated, it would lie outside the body unless specific adaptations were made thereto during fabrication in order to allow efficient introduction of subcomponent 96 into the body.

Figures 11A, 11B, 11C, 11D:
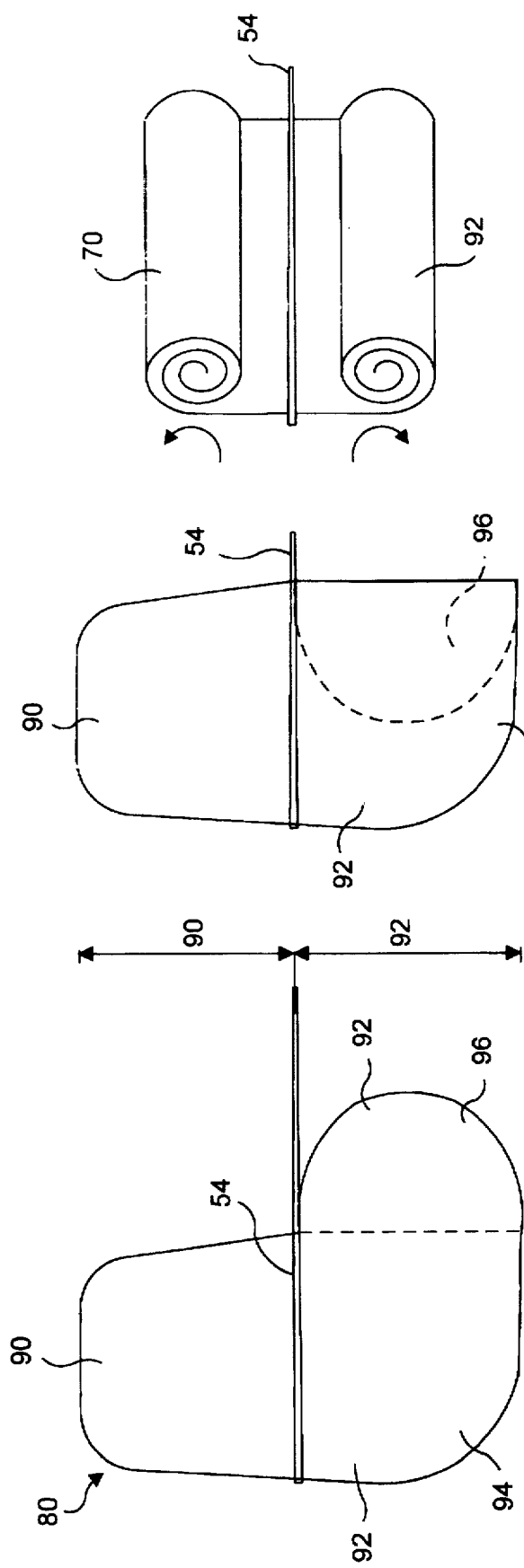
FIG. 11A is a schematic cross-sectional view of a balloon device in the uninflated or collapsed position prior to assembly and rolling.
FIG. 11B is a schematic representation of one of the wings of the balloon device of the present application being folded to lie inside another portion of the balloon device.
FIG. 11C is a schematic representation of the wings of the balloon device being rolled toward the guiderod or center axis.
FIG. 11D is a schematic representation of the balloon device collapsed, folded and/or rolled before deployment and/or inflation.

In the manufacture of the device, several steps are taken during fabrication to define the size and shape of the device in its non-deployed or collapsed state as well as to define its inflation behavior. After fabrication of the balloon part of the device and incorporation of the fill tube and either before or after attachment to the guiderod-handle-tip assembly, the balloon sits in a flat state, as illustrated in FIG. 11A. Subcomponent 96 of wing 92 is normally positioned posterior to the access incision. In order to introduce a portion of the balloon 50 under the skin, subcomponent 96 is inverted and folded such that it lies within subcomponent 94, as illustrated in FIG. 11B. Wing 90 and wing 92 are then rolled from their lateral extends toward the guiderod 54 or central axis, if no guiderod is used, as illustrated in FIG. 11C. When rolling is complete, a sheath can be added to preserve the device in the collapsed, folded, rolled configuration until deployment and/or inflation, which is illustrated in FIG. 1D. The device can be single use or reusable.

Figure 12:
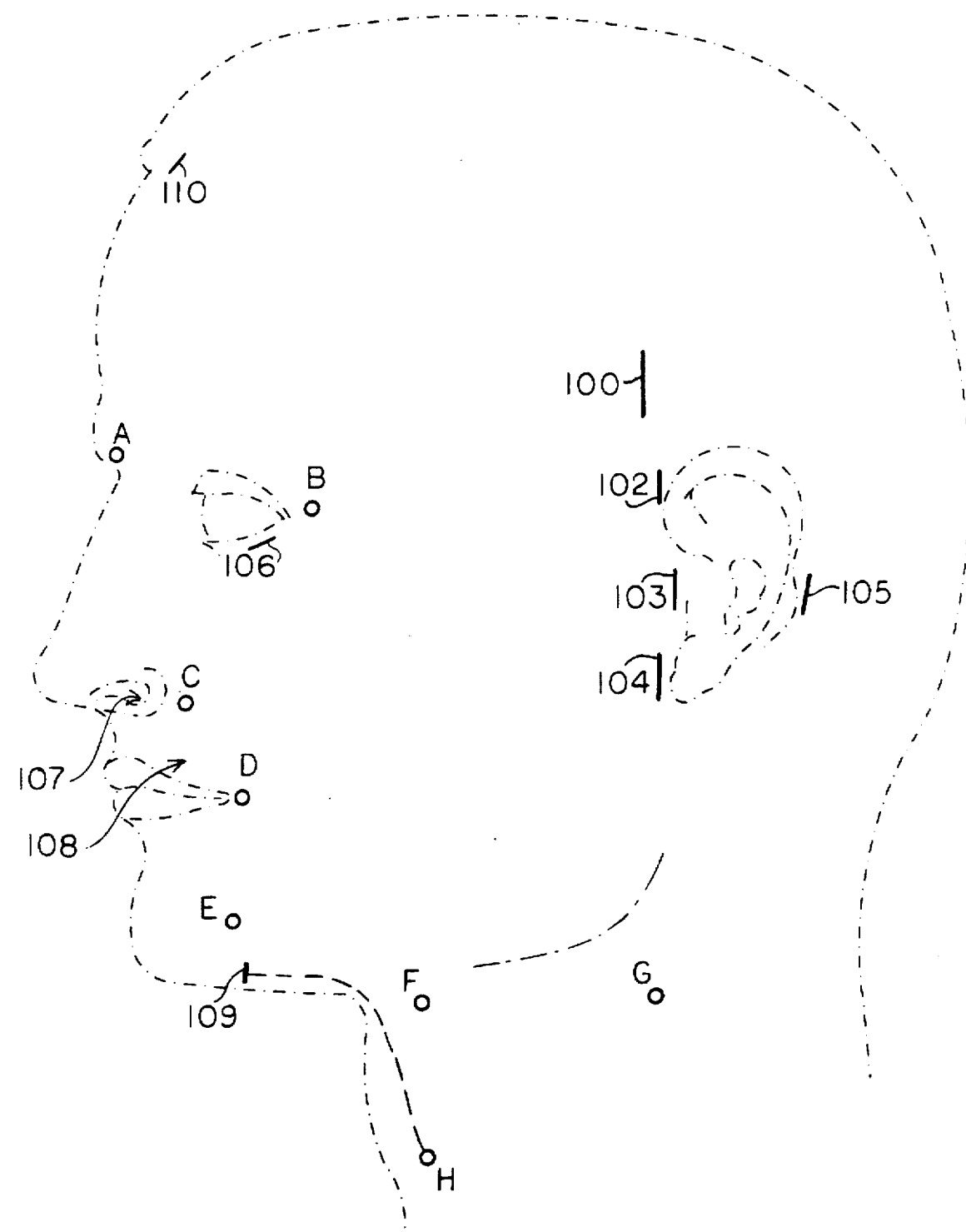
FIG. 12 is a side view of the face illustrating common access incision and aiming point options.

During insertion toward a normal insertion point of FIG. 12, all of wing 92 including subcomponent 96 will be introduced through the access incision and beneath the skin, if the inversion folding step is incorporated into the manufacture of the device. If reuse of the device takes place during surgery, such as in the instance where one device will be used for both sides of the face, the device can be refolded and rerolled, as in the initial manufacture. The rolling pattern can be identical on both sides in which case the device would unroll deep on one side and superficial on the other, or on rerolling, the surgeon can reverse the direction of rolling to allow deep dissection or superficial dissection on both sides of the face according to surgeon preference. It should be understood that the top and bottom of the panels used to make the balloon are identical, in the preferred embodiment. Once these panels are connected, they can be rolled on the appropriate side so that during deployment they are deployed against the superficial surface of the initial cavity. To reuse the same balloon for the opposite side of the face, it is necessary that the surgeon merely reroll the panels of the balloon after deflation and removal from the first cavity in the opposite direction. Alternatively, fabrication of a, for example, left sided balloon would require rolling of the panels in the opposite direction from the fabrication of a right sided balloon to allow both balloons to unroll against the superficial surface of the initial cavity.

Because the inflated balloon has a specific defined asymmetric geometry, positioning of the balloon on insertion and during inflation is critical to obtaining the desired tissue dissection. Methods for using the device of the present invention that produces the desired dissection in both depth and position includes using specific access incisions and specific endpoints to define the initial cavity or tunnel and/or tip of the balloon device. FIG. 12 is a sideview of the face that illustrates some options for access incisions and endpoints. As shown in FIG. 12, numbers represent possible locations of access incisions for practicing the methods and devices of the present invention. These points were selected to provide suitable locations that lie along the line of possible incision having minimal visibility or that are otherwise cosmetically acceptable. Access incision 101 represents a position along the line of traditional temporal facelift incisions that is superior to the root of the helix within the hair bearing scalp. Access incision 102 represents a position just superior to the root of the helix or alternatively in a preauricular position just at the root of the helix. Access incision 103 represents a preauricular incision position midway along the height of the ear or at the tragus. Access incision 104 represents a preauricular incision position at the inferior extent of the ear along the lobule and/or around and/or just behind the lobule. Access incision 105 represents an incision positioned in the retroaurcular sulcus. Alternatively, access incision 105 could be placed in the hair bearing scalp just posterior and superior to the region shown. Access incision 106 represents a lateral canthal or subciliary incision. Access incision 107 represents an intranasal incision along the pyriform aperture. Access incision 108 represents an intraoral incision in the gingival buccal sulcus. Access incision 109 represents a submental incision. Access incision 110 represents a midline scalp incision behind the anterior hairline. In general, those access incisions are each between about 1 and about 2 cm in length, although they can be longer or shorter.

Also, as shown in FIG. 12, lettered items represent aiming points for dissection of the initial cavity or tunnel and represent endpoints for insertion of the tip of the balloon device. Aiming point A is shown at the nasal root just inferior to the glabella. Aiming point B is shown at the lateral canthus or bony lateral orbital rim. Aiming point C is shown at the lateral base of the ala along the nasolabial groove. Aiming point D is shown as the modiolus or lateral corner of the mouth. Aiming point E is shown as the mental foramen of the mandible or a point midheight along the body of the mandible medially at the anterior/medial most desired point of dissection. Aiming point F can be located anywhere in the submandibular portion of the neck at the anterior most point of desired dissection. Aiming point G is shown as located at the angle of the mandible. Alternatively, aiming point G can be located at any point directly inferior to the angle of the mandible at the inferior extent of desired dissection. Aiming point H is shown located over the midpoint of the hyoid bone or the thyroid cartilage depending on the extent of desired dissection.

Various permutations and combinations of access incisions and endpoints are possible depending on the intended plane and desired geometry of dissection. Some preferred combinations are specifically listed below. It should be understood that the list is not exhaustive but represents only some possible combinations usable with the methods and devices of the present invention.

Figure 13:
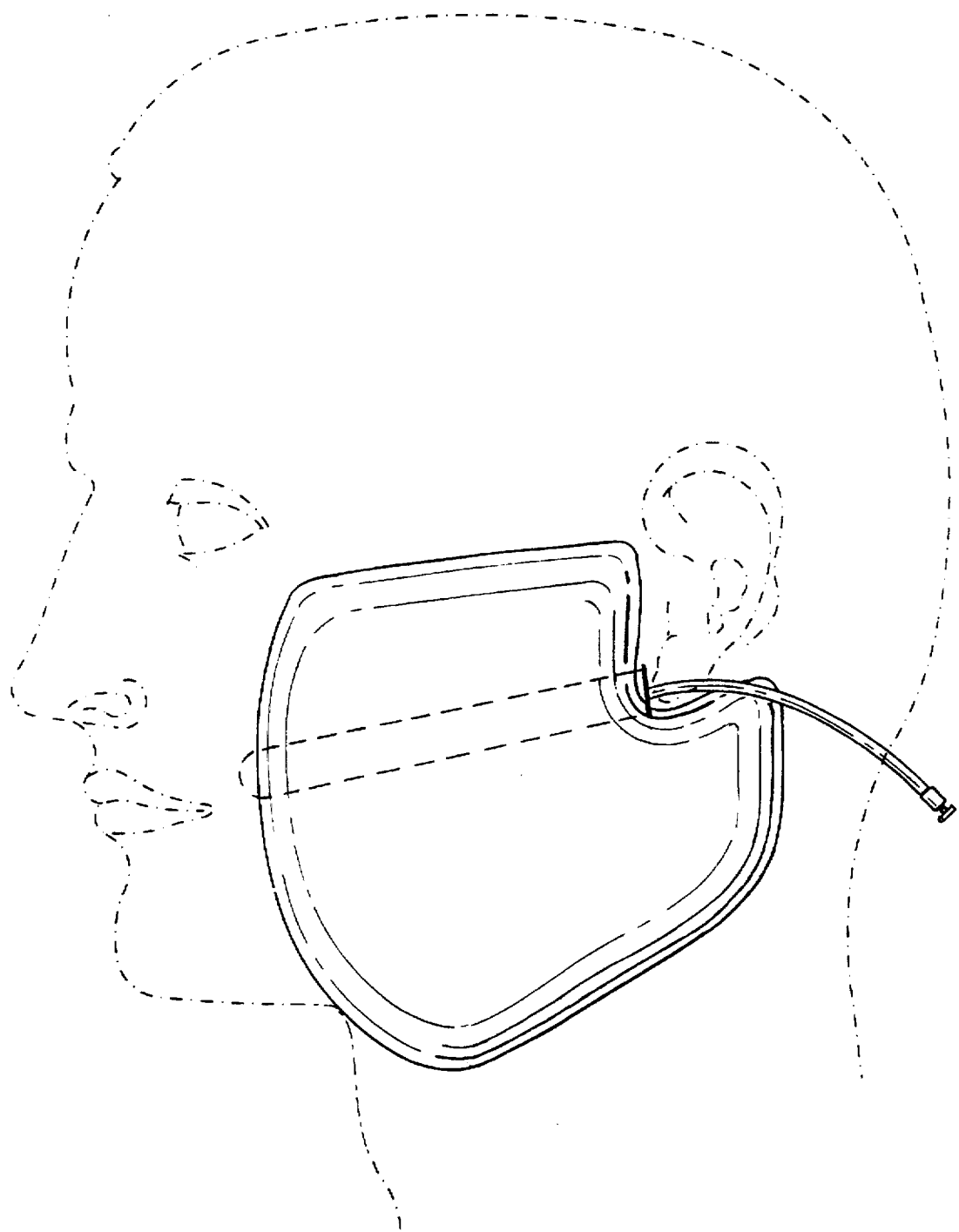
FIG. 13 is a schematic representation of one preferred embodiment of the present invention deployed and inflated inside a human face.

FIG. 13 is illustrative and represents one preferred embodiment of the present invention. A lateral view of the face illustrates the access incision 104 in the preauricular region by the lobule. After creation of the access incision at point 104, dissection would proceed toward point D at the modiolus or lateral corner of the mouth. This dissection could be accomplished sharply, bluntly or with energy delivery devices (cautery, laser, etc.). The depth of the initial cavity must be precisely controlled by the surgeon in order to position the device within the tissue such that dissection of the remainder of the final cavity is at the desired depth within the tissue. The initial cavity or tunnel 44 is illustrated by the dotted line in FIG. 13.

Once an initial cavity of adequate length and width is created at the appropriate depth, the device is inserted in the appropriate position within the initial cavity. The correct length of insertion of the device would allow complete introduction of the rolled, folded balloon assembly into the initial cavity, directing the tip of the device through the access incision pointing toward the endpoint. During insertion, the balloon must be maintained in the correct orientation due to the asymmetric wings. Indications can be placed on the sheath, guiderod 54 or handle 58 in order to facilitate accurate positioning. Finally, once precisely positioned, the balloon is inflated through the fill tube that is extending out of the access incision until the desired extent of dissection is produced to form the final cavity 120. The planned position of the balloon 50 after inflation is illustrated by the solid balloon outline in FIG. 13.

One of the major obstacles to balloon dissection overcome by the features of the present invention is clearly illustrated in FIG. 13. As known, incision placement is extremely limited by the desire to have minimal incisions and by cosmetic considerations of suitable or possible incision locations especially on the face. As earlier discussed, the face also has multiple anatomic structures that serve as barriers to tissue dissection. These barriers include the nose 122, eyes 124, mouth 126 and ears 128. Specifically, facelift dissection must be performed both in front of and behind the ear 128. With an access incision at one location, it is difficult to provide dissection in front of, below, behind and above the access incision with the ear 128 acting as an obstacle. Difficulty in introducing a balloon of the appropriate size and shape into an initial cavity in a way that will allow easy inflation and successful balloon dissection is another challenge overcome by the present invention. By folding the postauricular component of the balloon into the submandibular component, introduction and deployment of a single balloon through a single incision that will perform the majority of required facelift dissection is accomplished and provides for preauricular/cheek and submandibular dissection to be accomplished first followed by postauricular dissection as the inverted postauricular subcomponent of the balloon unfolds after unrolling of the lateral wings of the balloon.

Figure 14:
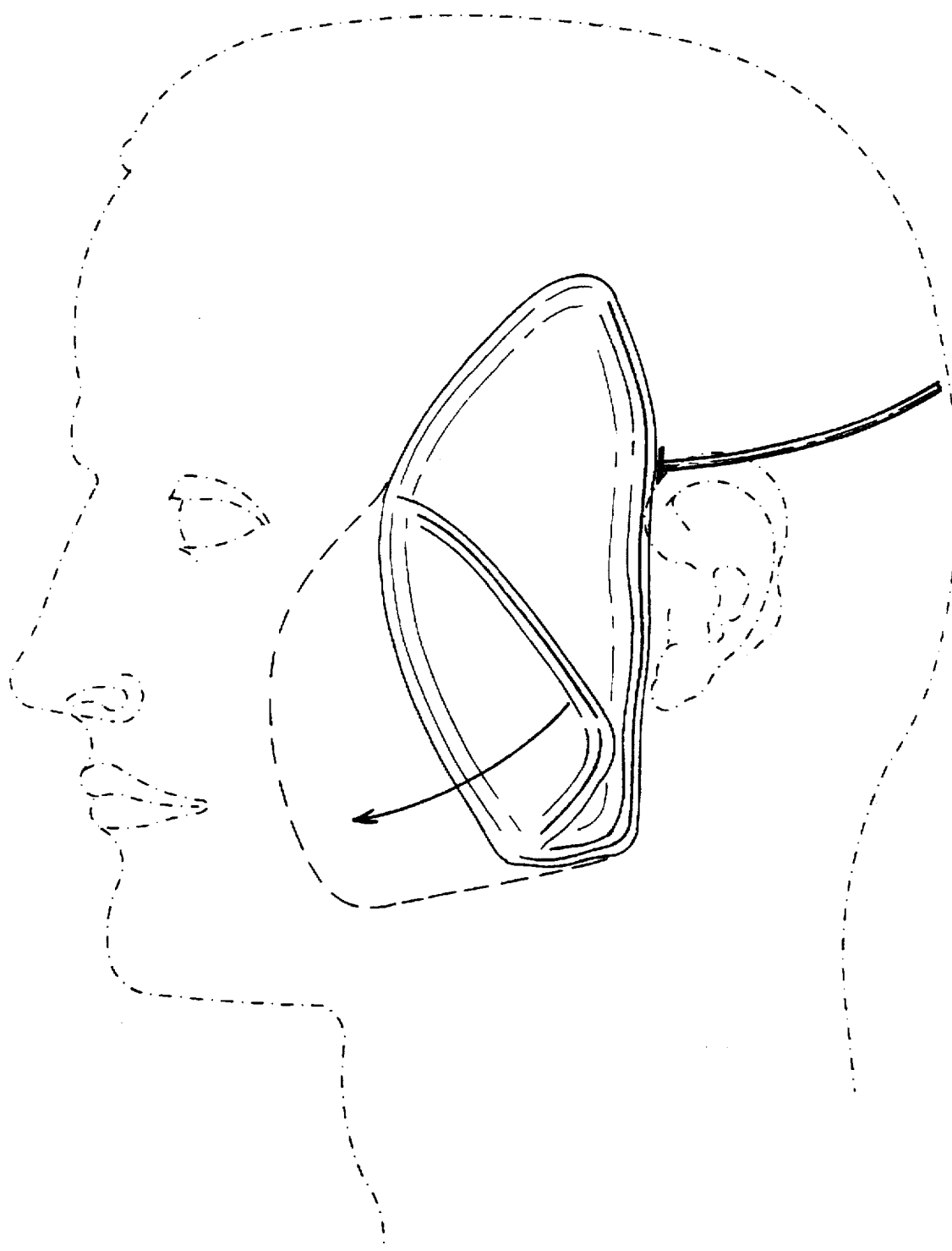
FIG. 14 is a schematic illustration of the balloon dissection propagating device used to dissect the temporal and cheek portions during a facial dissection.
Figure 15:
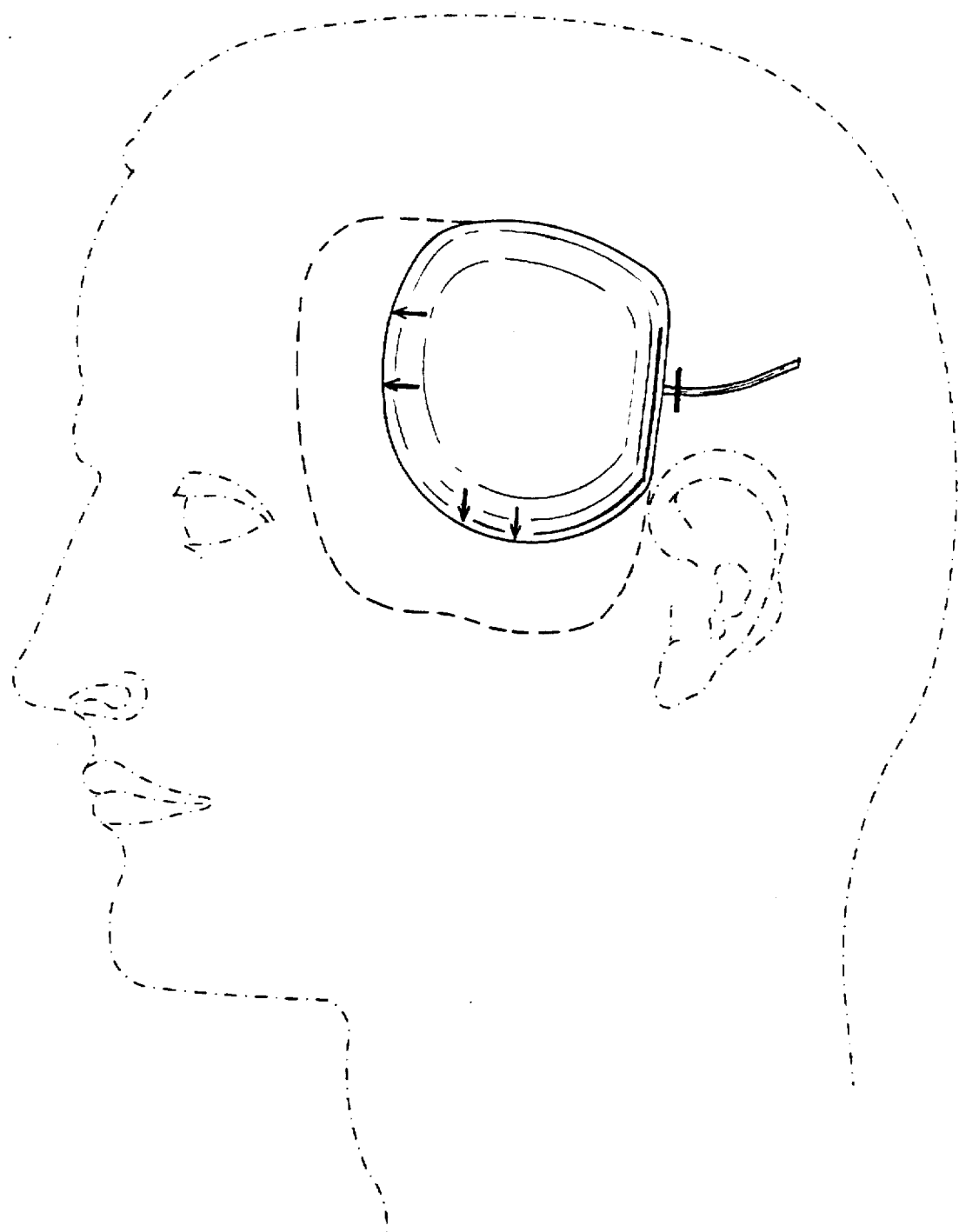
FIG. 15 is a schematic illustration of a smaller balloon which could be used to dissect the temporal portion of the face.

As illustrated in FIG. 12, other preferred incision/ endpoint combinations include 101 and B, 102 and B, 102 and C, 103 and D, 104 and C, 104 and D, 104 and E, 104 and F, 104 and G, 105 and F, 105 and G, 107 or 108 toward incisions 101–104, 109 and H, 110 and A, among others. It should be apparent that other balloon dissection strategies exist in addition to those illustrated which would use the preferred devices and methods and are intended to be specifically incorporated into this application as additional methods of facelift balloon dissection. These additional methods and devices include use of separate balloons for dissecting specific portions of the facelift dissection or to dissect different planes of the facelift dissection. Examples would include subperiosteal dissection of the cheek portion through incisions 106–108 in FIG. 12. Dissection of the scalp subperiosteally or subgaleally or beneath the superficial temporal fascia through incisions 101, 102, 106 and 110. Incisions 101 and 102 can also be used to dissect the temporal or cheek portion in the subcutaneous plane. FIG. 14 illustrates the use of a single balloon introduced through incision 101 to dissect the temporal and cheek portion of the facial dissection. The devices as illustrated could unroll with two lateral wings about the axis between incision 102 and point B and then unfold further medially into the cheek area of the inferior wing. Through incision 101 a smaller balloon could be used to dissect the temporal portion of the facelift as illustrated in FIG. 15. The device utilized could be an unrolling, unfolding or expanding balloon.

Figure 16:
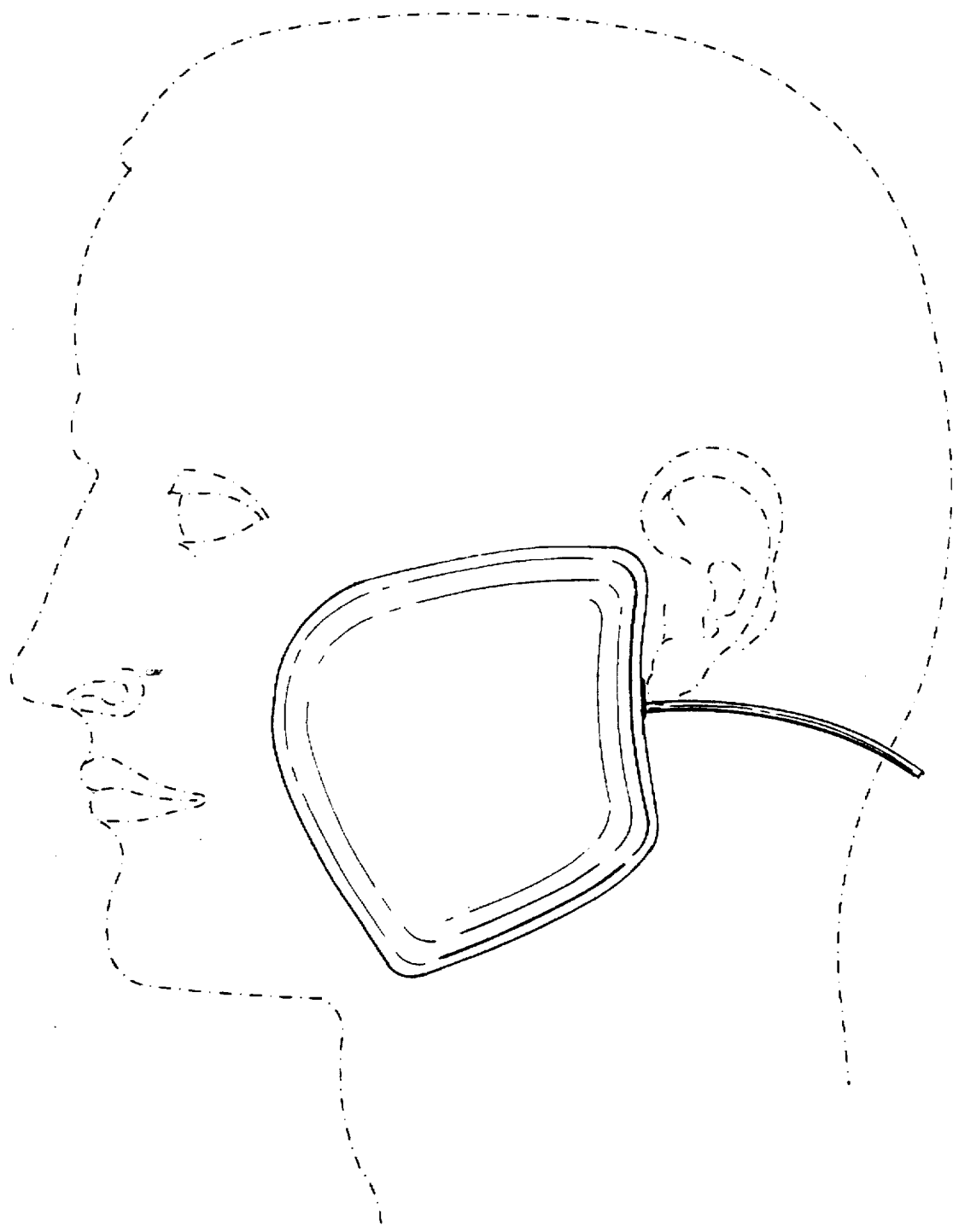
FIG. 16 is a schematic illustration of another embodiment of the balloon that could be utilized to dissect the facial portion in the subcutaneous plane during a facelift procedure.
Figure 17:
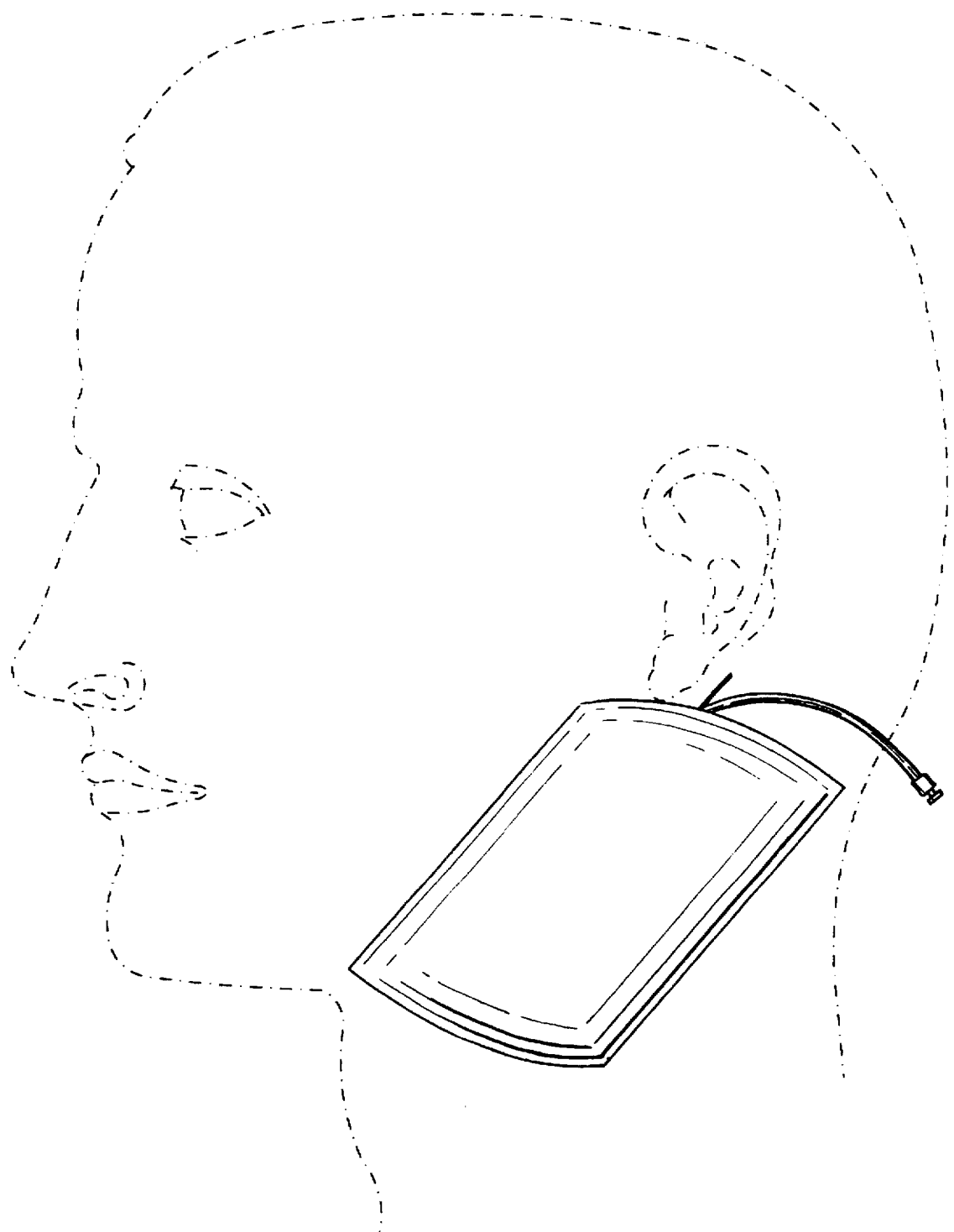
FIG. 17 is a schematic representation of the dissection of the neck portion of the facelift dissection.
Figure 18:
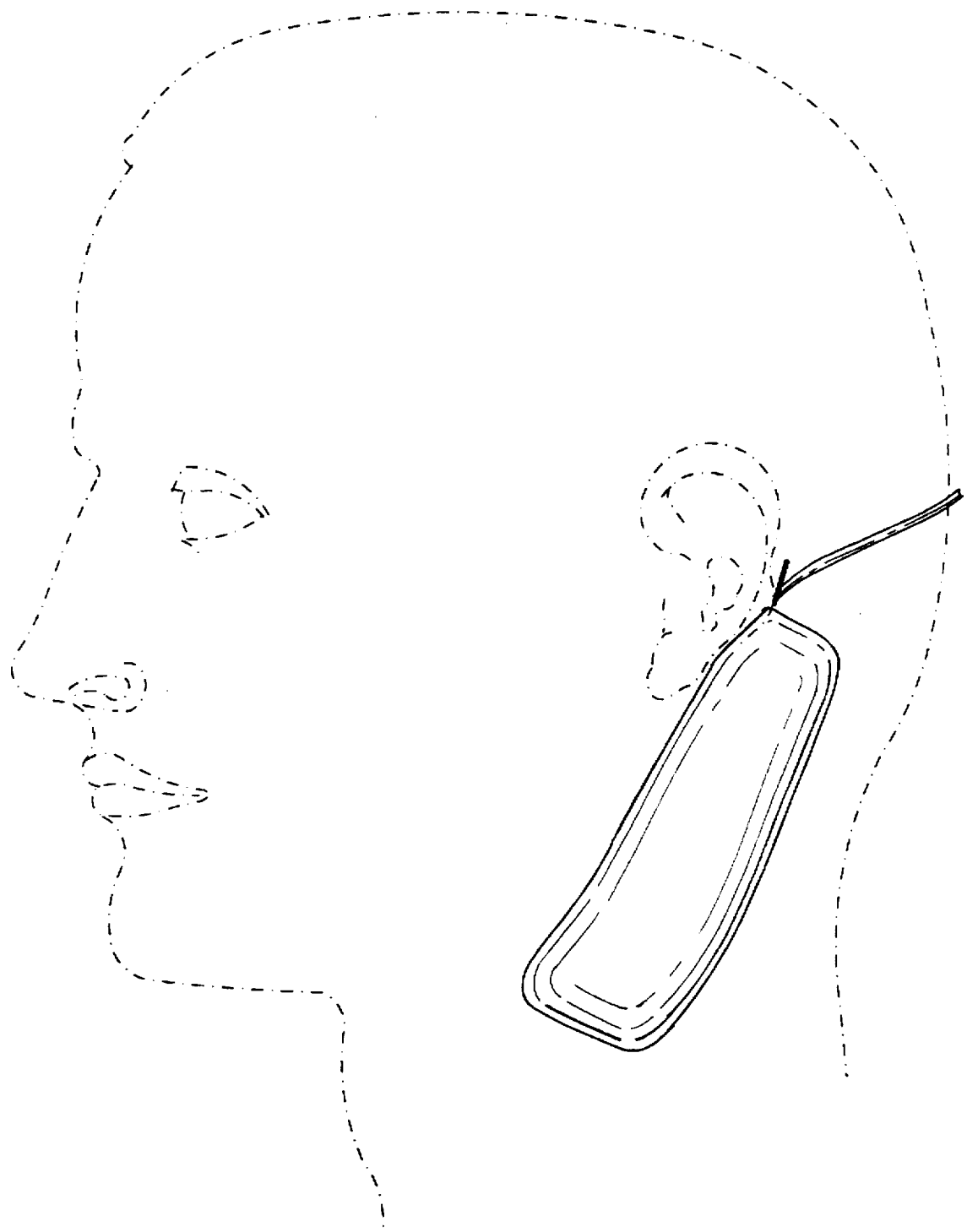
FIG. 18 is a schematic representation of an retroauricular dissection which could be performed using the dissection propagation device of the present invention.
Figure 19:
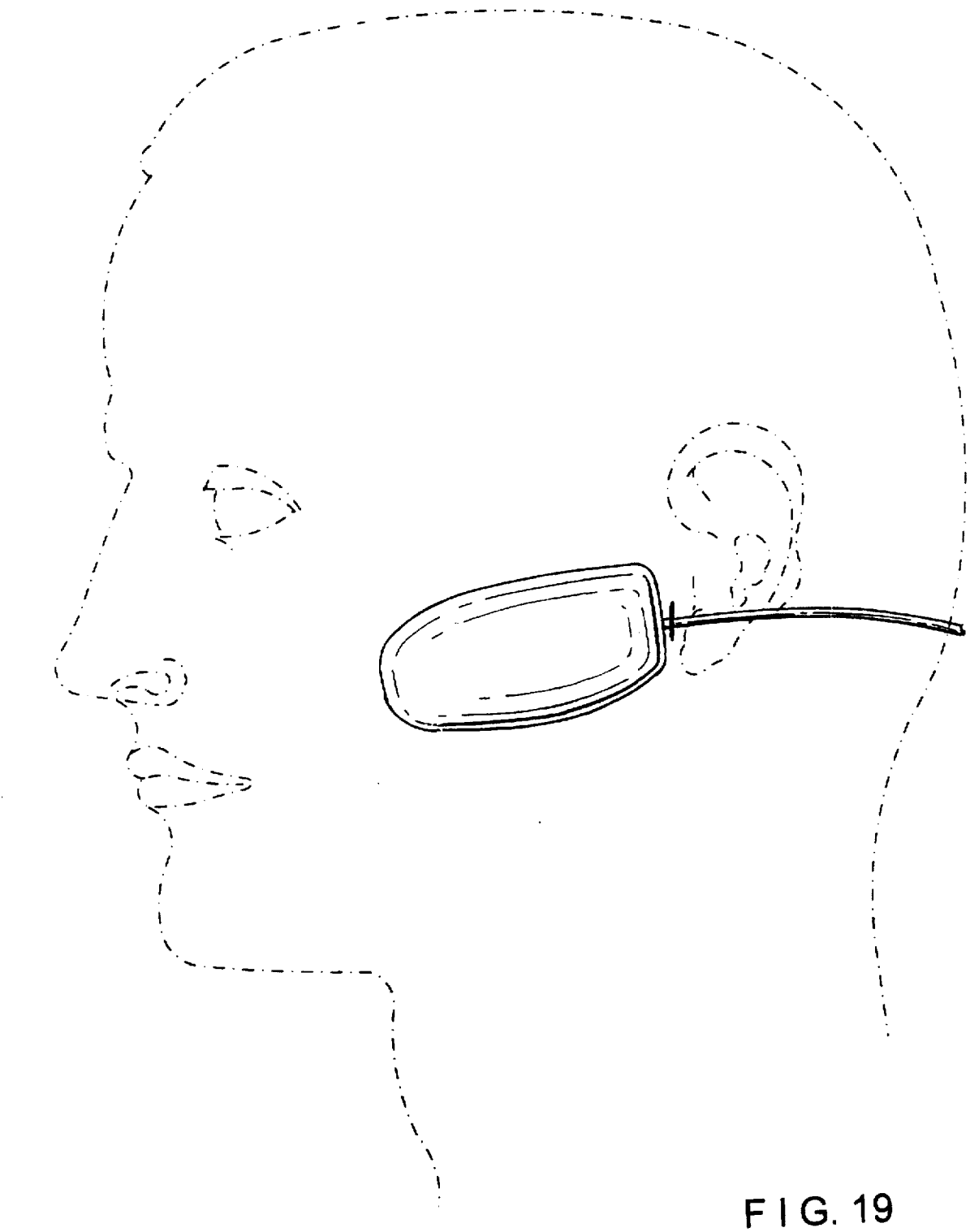
FIG. 19 is a schematic illustration of a dissection of the cheek area utilizing a balloon device of the present invention.
Figure 20:
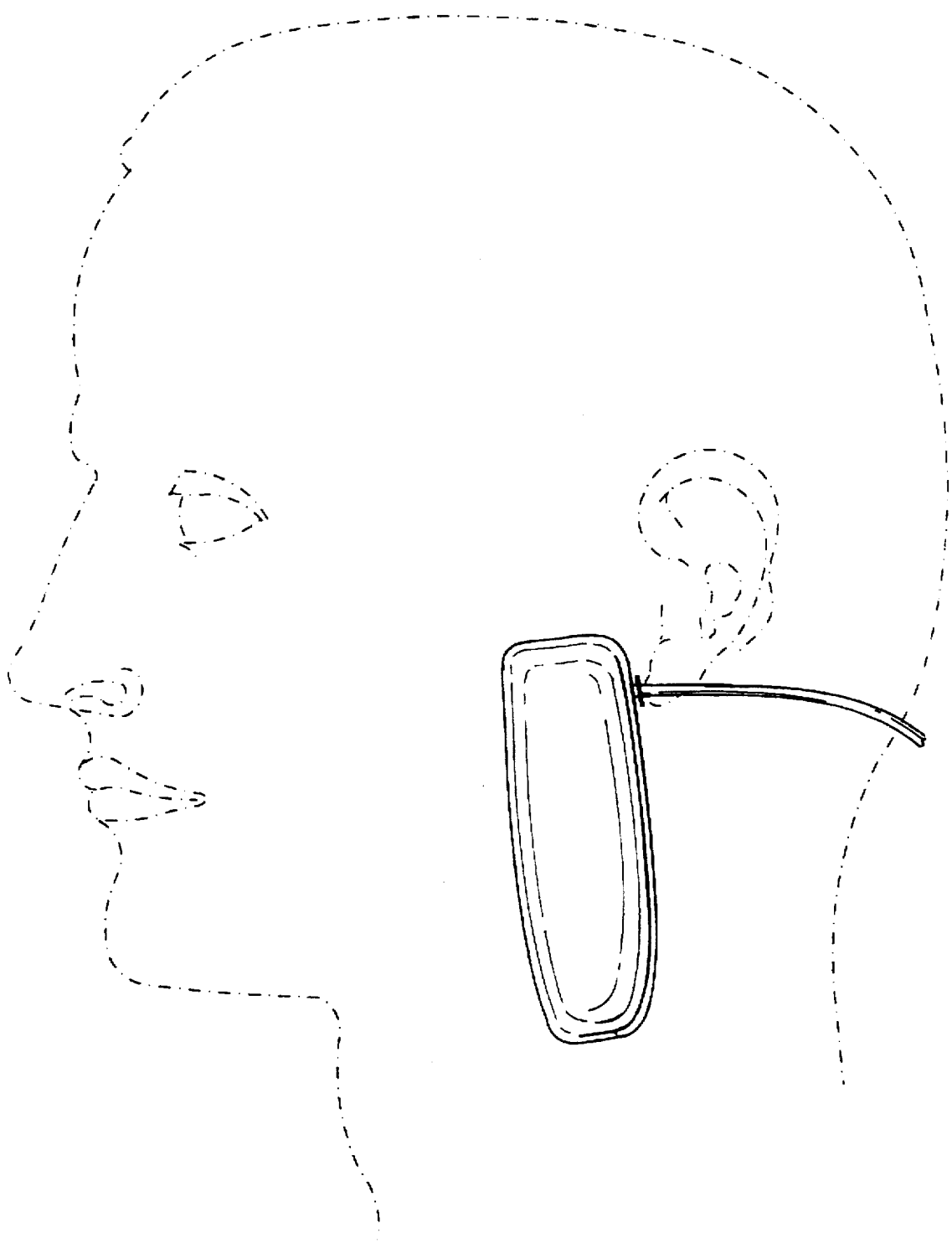
FIG. 20 is a schematic illustration of the utilization of a balloon device for dissection of the platysma area in the neck.

In another embodiment, a balloon could be inserted through incision 103 or 104 toward point D, E or F to dissect the facial portion in the subcutaneous plane as illustrated in FIG. 16. This approach could be used alone or in combination with an additional balloon to dissection the neck portion of the facelift dissection. The neck portion dissection could be performed with a balloon inserted through incision 104 or 105 directed toward points F or G, as illustrated in FIG. 17. Retroauricular dissection could be performed through incision 105 directed toward point G, as illustrated in FIG. 18. The SMAS flap could be elevated using balloon dissection as well. This elevation could be performed using one balloon device for the cheek area, as illustrated in FIG. 19 and another balloon device for the platysma in the neck as illustrated in FIG. 20.

In patients requiring submentalplasty either at the time of facelift or as a stand alone procedure, a balloon device could be inserted through incision 109 toward point H, as illustrated in FIG. 7. Possible dimensions of such a balloon are about six (6) to about eight (8) cm long by about six (6) cm wide. Such a balloon device would be designed to dissect in the submandibular area down to the hyoid bone or thyroid cartilage and laterally to the sternocleidomastoid muscles.

Figure 21:
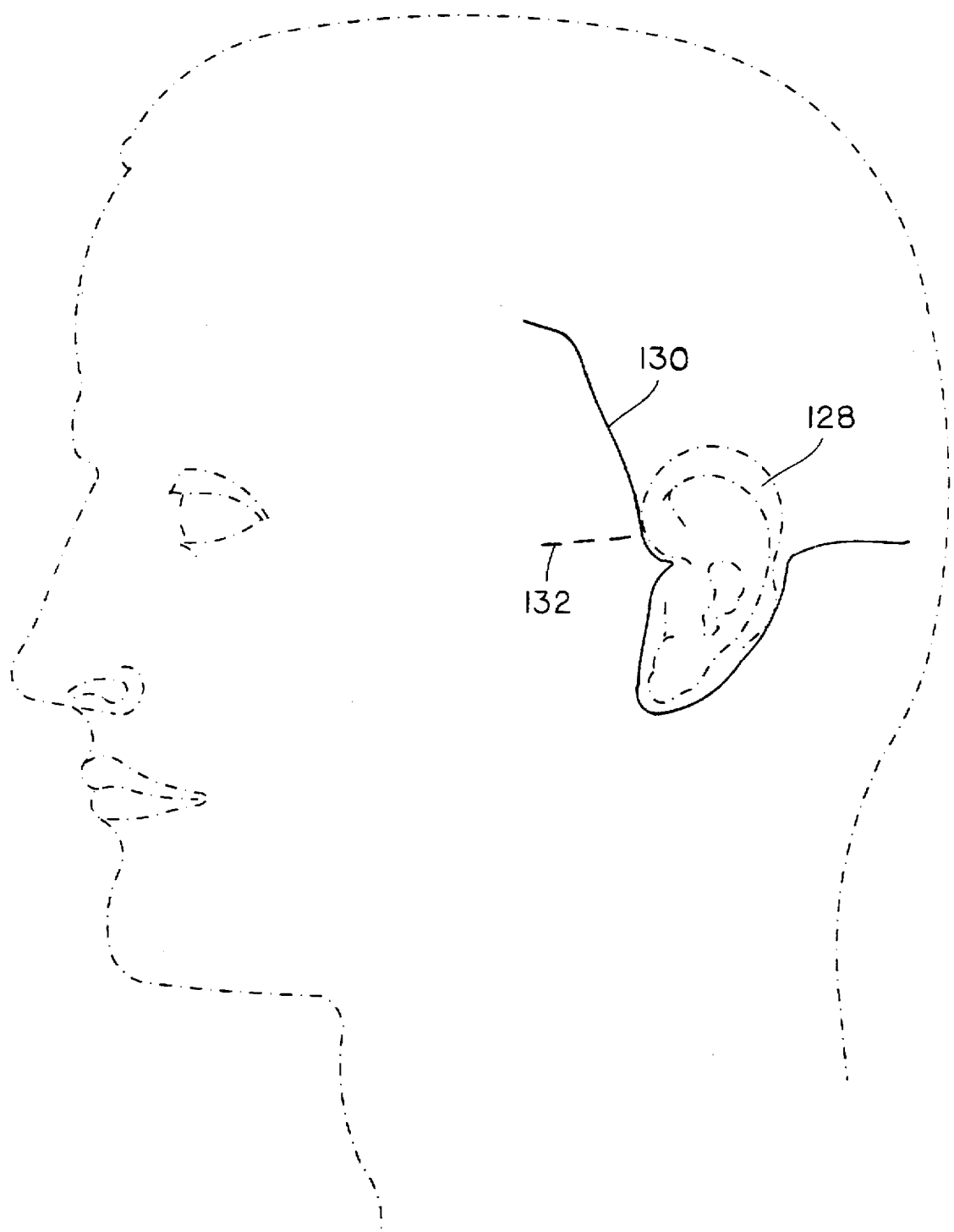
FIG. 21 is a schematic illustration of the conventional facelift incision.

As is known, in facelift surgery, the dissection of the skin flap is only one portion of complex procedure. Once the final cavity has been formed by the dissection propagating device, it is necessary to sever the skin flap along the conventional facelift incisions 130 that start in the temporal hairline and extend inferiorly in the preauricular (in front of the ear 128) skin around the lobule (earlobe), posteriorly and superiorly in the retroauricular sulcus (the skin behind the ear) and then posteriorly into the hairline at the level of the tragus or the root of the helix as illustrated in FIG. 21. The broken line 132 represents an additional optional incision that can be made in the lower border of the sideburns hair (present even in women).

Figure 22:
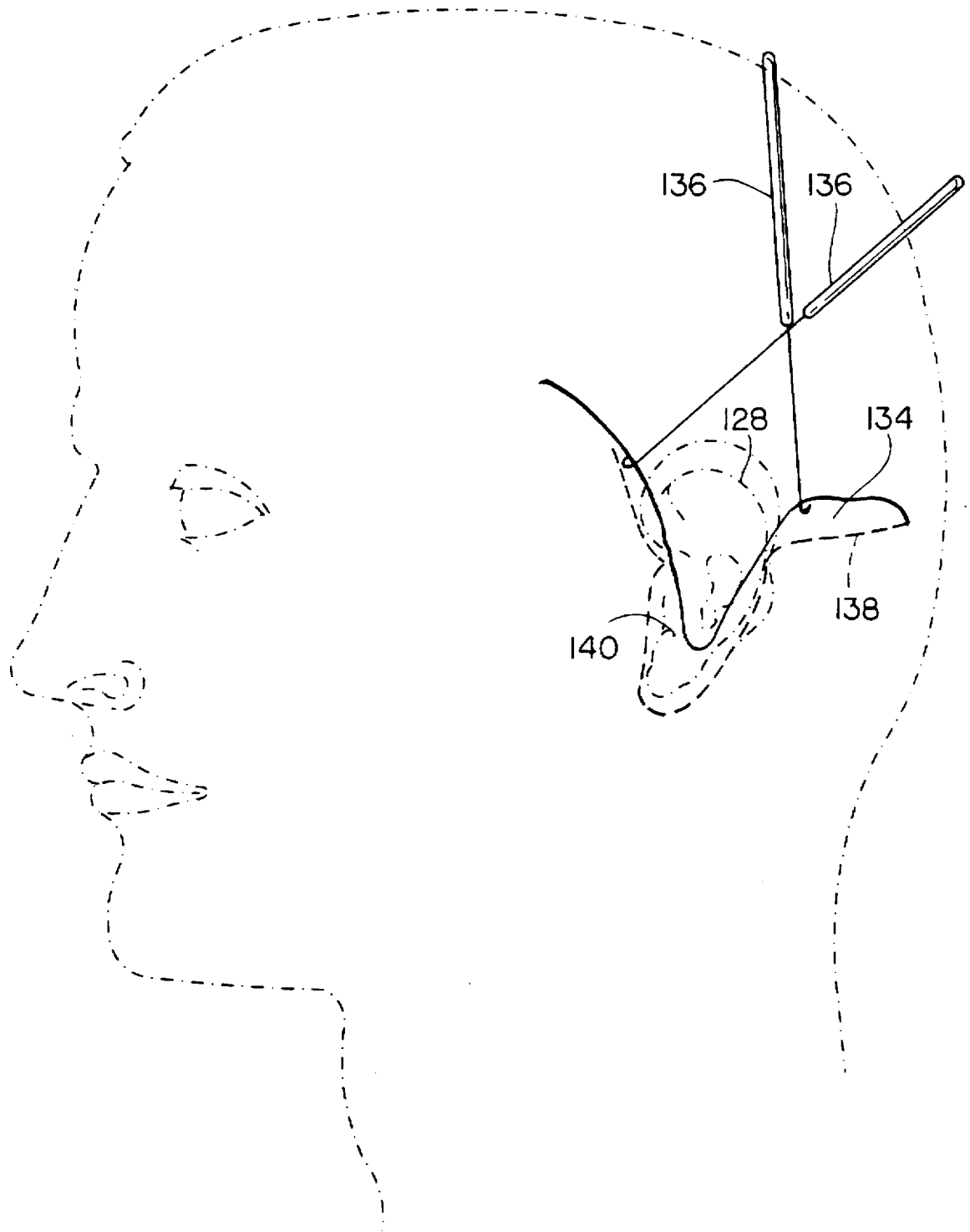
FIG. 22 is a schematic illustration of the facial and neck skin being redraped or placed on tension with skin hooks.

FIG. 22 illustrates the facial and neck skin 134 being redraped or placed on tension with skin hooks 136 to take any slack out of the face. The initial skin incisions are shown by the dashed line 138. After the skin flap has been redraped, the excess skin 140 would be trimmed at the dashed lines in order to remove skin overlapping the ear 128 and posterior hair.

Figure 23:
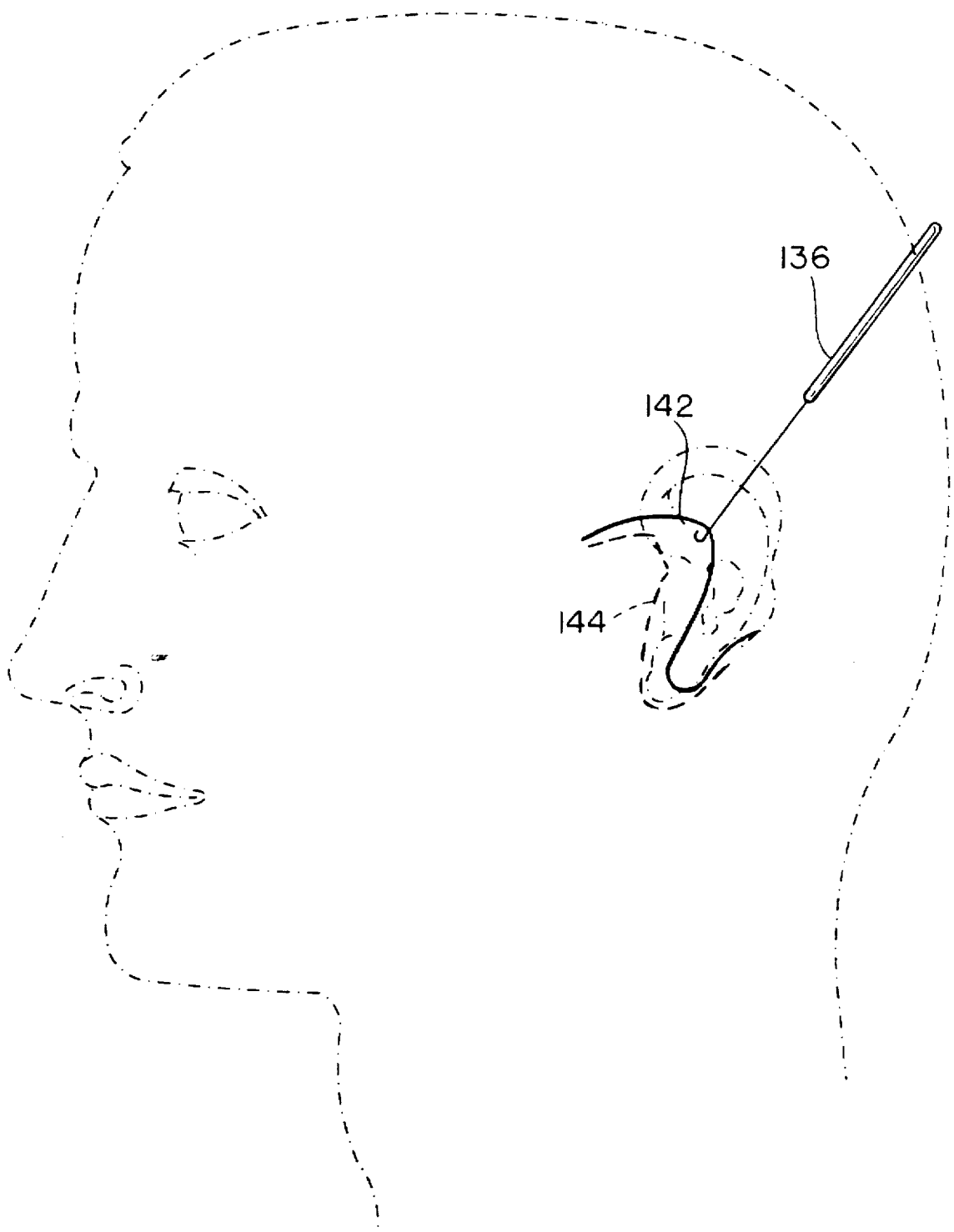
FIG. 23 is a schematic illustration of skin removal in a preauricular incision to allow removal of a triangle of skin in the preauricular area.

FIG. 23 illustrates skin removal in a preauricular incision with the additional transverse sideburns incision of FIG. 21 to allow removal of a triangle of skin 142 in the preauricular area. This excision allows both vertical and horizontal redundancy (excess skin) to be removed. The dashed line represents the initial skin incision with the overlapping skin (solid line) placed on tension by a skin hook 136.

Figure 24:
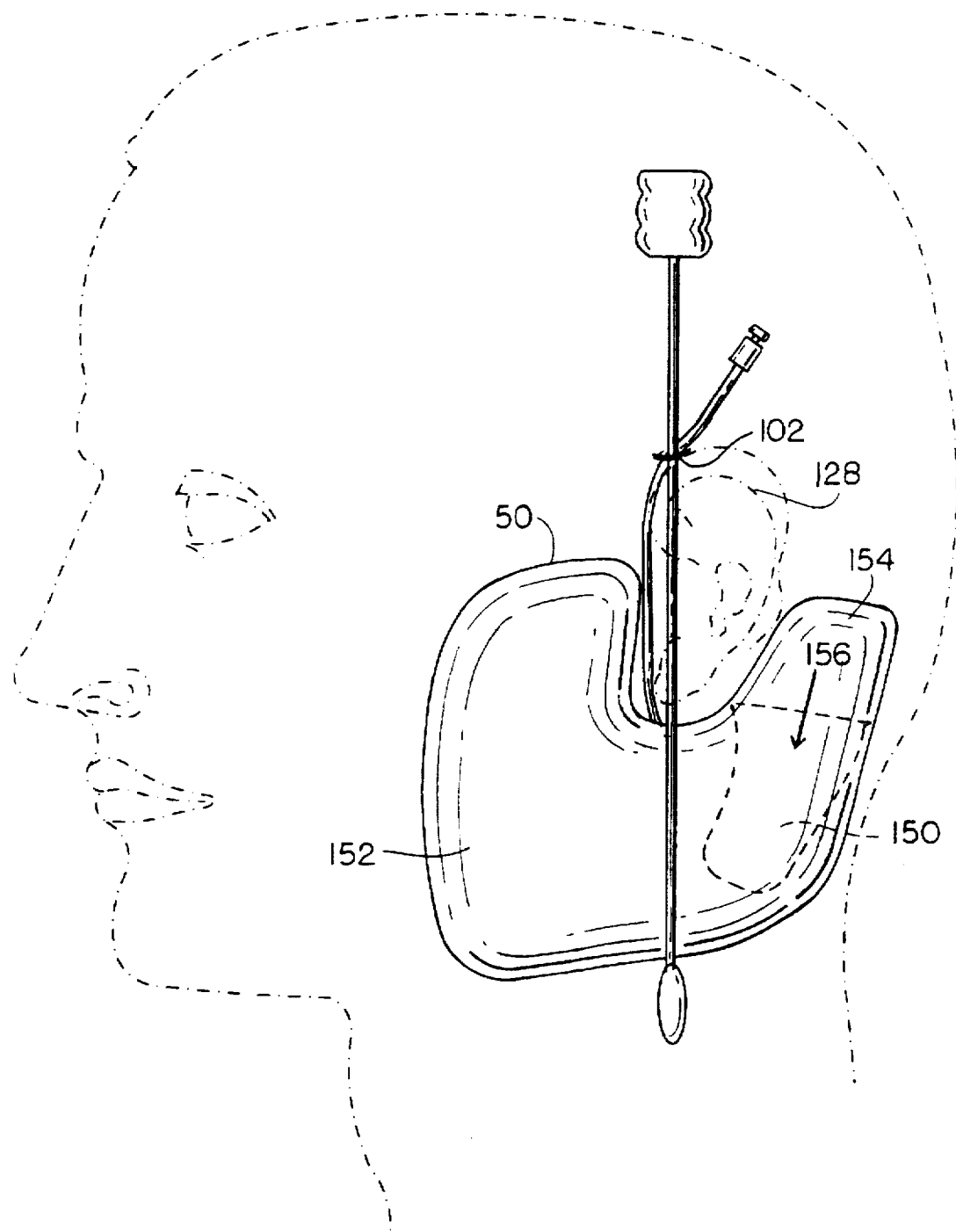
FIG. 24 is a schematic illustration of an alternative balloon dissection propagating device of the present invention having asymmetric wings and including a portion of the balloon folded within one of the wings.

FIG. 24 illustrates another possible embodiment of a balloon facelift dissector device having asymmetric wings 150, 152 including a portion 154 of the balloon 50 folded within one of the wings 150. The dissection propagating device is inserted through a skin incision 102 at the tragus or alternatively at the root of the helix. The tunnel or initial cavity is created toward point G (see FIG. 12). The medial wing of the balloon unrolls from the preauricular to the nasolabial area, lateral to medial, dissecting the cheek and preauricular neck. The lateral wing 150 unrolls/deploys in the neck area. Once the lateral wing is fully unrolled/ deployed, a vertical component 154 deploys which has been folded within the subauricular portion of the balloon. This vertical component 154 telescopes superiorly dissecting the retroauricular/posterior portion of the facelift dissection. The broken line 156 represents the level at which the vertical component is folded within the lateral wing, indicated by the arrow.

This particular dissection propagating device provides for dissection in front of and behind the ear 128 without the necessity of placing an incision on the face or outside hair bearing skin. The obstacle of the ear 128 is circumnavigated by the balloon portion of the device that creates the desired dissection in the appropriate plane both in front of and behind the ear 128.

Figure 25:
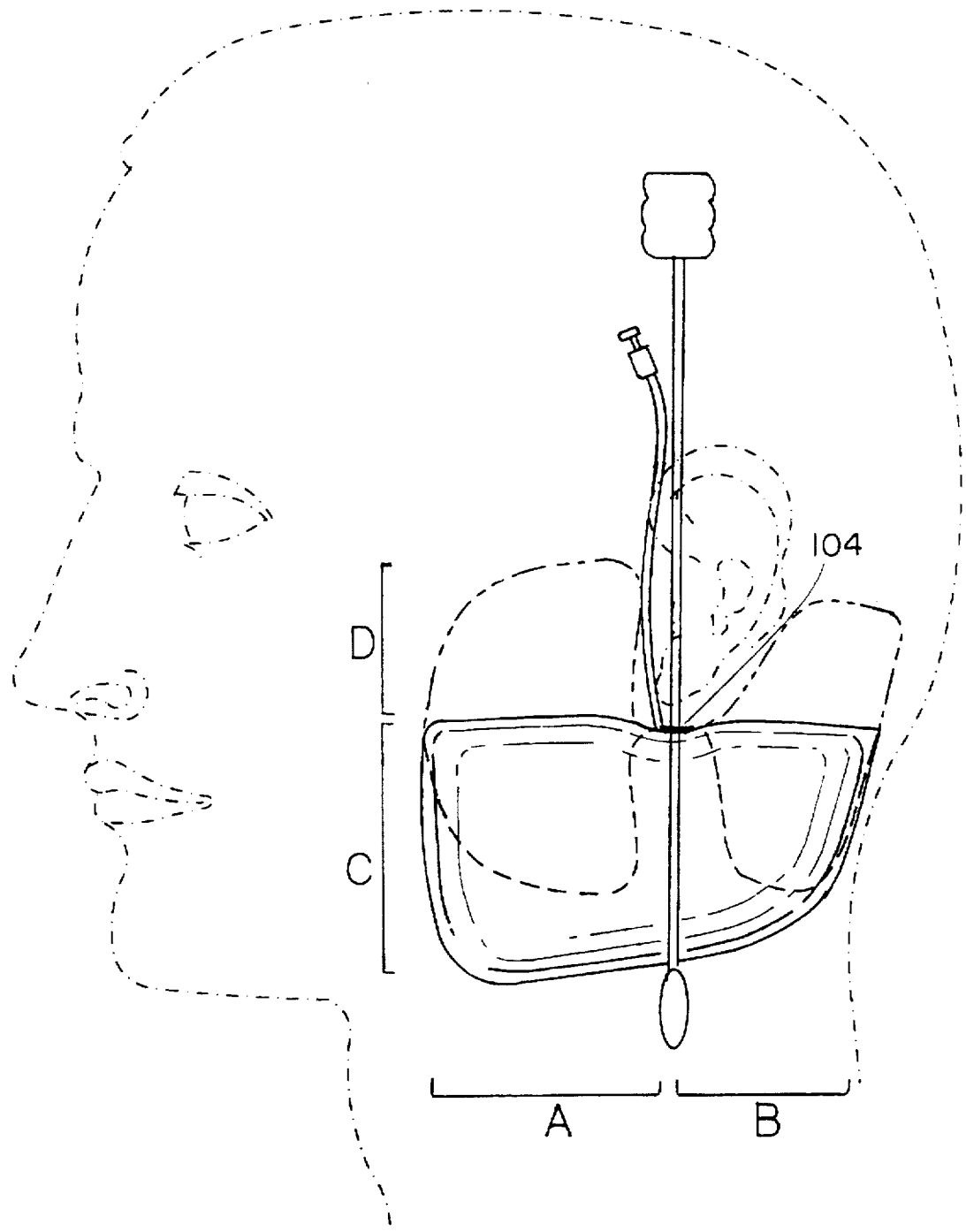
FIG. 25 is a schematic illustration of an alternative balloon dissection propagating device of the present invention having two asymmetric wings and including one portion folded within each of the wings.

FIG. 25 is an illustration of another alternative embodiment of the present invention. The device is inserted at the base of the lobule just in front of or just behind or just at the inferior rim of the lobule. Wings A and B unroll from the central axis or from the guiderod of the device. Wings A and B dissect the preauricular, mandibular and the post auricular area respectively, collectively comprising the subauricular portion of the facelift dissection. After completion of unrolling of the wings A and B, the re-entrantly tucked portions unfold superiorly to complete dissection of the cheek and retroauricular areas. Area C is the area dissected by the unrolling wings A and B collectively comprising the subauricular portion of the facelift dissection. Area D is the portion of the dissection required above the lobule comprised of the cheek and retroauricular portions of the dissection which are formed by the folded portions of wings A and B respectively. This embodiment illustrates the features of dissection back past the point of insertion along the axis of insertion as well as dissection around an anatomical obstacle. Each wing of the device has a folded portion. Wings are asymmetric due to the shape and size of the dissection required for the facelift.

Figure 26:
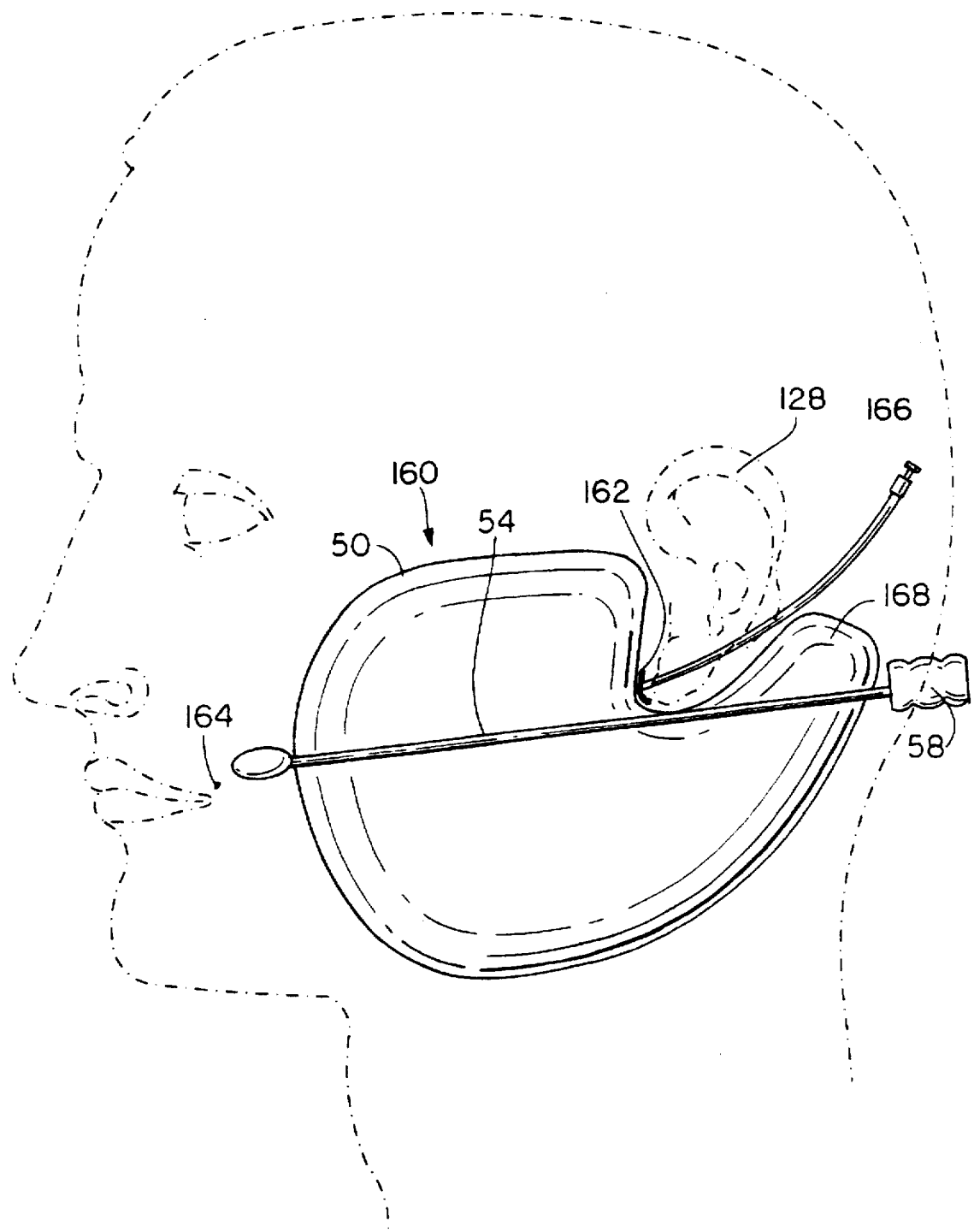
FIG. 26 is a schematic illustration of the preferred embodiment of the facial plasty dissection propagating balloon device of the present invention shown in the inflated condition positioned in the face of the patient.

FIG. 26 is an illustration of the preferred embodiment of the facialplasty dissection propagating balloon device 160 of the present invention. The device 160 is shown as being inserted through a small (1–2 cm) incision 162 at the lobule (earlobe) and aimed toward the modiolus or lateral corner of the mouth or oral commissure 164. A fill port 166 is operatively connected to the balloon and is positioned proximate to the guiderod 54. The guiderod 54 provides for the easy introduction of the balloon 50 into the initial cavity (not shown), as well as stabilizing the device during the balloon inflation step. As shown, the neck wing 168 of the balloon produces dissection both posterior to the point of insertion as well as superior to the mid-axis of balloon that is at the level of the guiderod 54. This particular dissection is unique because such dissection has not been produced using prior balloon methods or devices. Dissection extending along the axis of the device proximal to the level of insertion has not been previously produced and, thus, is unique to the device and method of the present invention. This "backwards" dissection past the insertion incision toward the handle 58 of the guiderod 54 but in the predetermined plane within the tissue extends the scope and capability of the balloon dissection propagating devices propagation of the present invention. Dissection across the axis of the balloon device by at least one portion of the balloon is also a unique feature. Both unique features provide dissection forces that produce the desired dissection within the tissue without producing dissection within the tissue where dissection is not wanted. This controlled dissection is achieved despite the additional dissection constraints of having to avoid anatomic obstacles, such as, for example, the ear 128 by designing the balloon portion of the device so that certain predetermined areas are not violated by the balloon dissection propagating device.

The above devices and methods differ from previous balloon techniques in that the surgeon first creates a specific artificial tissue plane by tunnel creation or other means that is propagated by appropriate placement and deployment of dissection propagating devices such as, for example, balloon device. One specific improvement of the present invention includes a set of balloon designs and shapes that are adapted for specific application to the facelift procedure.

In a representative facelift procedure, only about eighty (80%) to about ninety (90%) of the final cavity is typically achieved by the balloon dissection propagating device with the remainder being accomplished by the surgeon. However, considerable operating time is saved and many potential complications are avoided by using the dissection propagating devices and the methods of the present invention as compared to the prior devices and methods for performing these surgical procedures.

As can be seen, utilization of the devices and methods of the present invention for facelift flap creation has met the objects of the invention and has many advantages over prior devices and methods. Specifically, less time and surgical skill is required to produce the necessary artificial tissue plane to elevate the facelift flap; less bleeding is created during the balloon dissection as compared to sharp dissection; less tissue trauma is created as forces on the skin are more widely distributed by the balloon as compared to utilization of sharp techniques and high power density energy introduction produced by cautery or laser devices; surgical operation time is significantly reduced; a softer flap with less swelling and bruising post-operatively results; a shortened recovery time is required; risk of skin loss is also reduced; risk of nerve injury is reduced; hemostasis time is reduced and additional skin may be removed without increasing the tension on the suture lines due to the intra-operative tissue expansion effect produced by the balloon.

Changes and modifications in this specifically described embodiment can be carried out without departing from the scope of the invention that is intended to be limited only by the scope of the appended claims.

What is claimed is:

1. A system including an inflatable means for use in cosmetic surgery to expand an initial cavity into a predetermined region of fatty-tissue cleavage extending transverse to the initial cavity to form a final cavity, the system comprising:

an elongate means having spaced proximal and distal ends and adapted at its proximal end to receive an inflation fluid and having at least one port at a location distal to the proximal end for supplying inflation fluid to the inflatable means;

the inflatable means comprising two like panels of pliant but essentially non-stretch material conforming generally to a predetermined region within a fatty-tissue cleavage and secured to the elongate means along a longitudinal alignment distal with respect to the proximal end and otherwise peripherally secured to each other, such that the port is in communication with the inflatable means;

the inflatable means being capable of initially being in an uninflated state wherein the inflatable means is precoiled and operatively connected to the elongate means;

whereby, upon insertion of the system into the initial cavity, the inflatable means is capable of conforming to an inflated state, wherein in the inflated state, the inflatable means is capable of expanding within a fatty-tissue and throughout an area within a fatty-tissue which is laterally offset with respect to the system such that when the inflatable means is inflated, the inflatable means deploys in a pattern that permits the inflatable means to remain in the initial plane within a fatty-tissue to form a final cavity within a fatty-tissue which conforms substantially to the predetermined region.

2. A system including an inflatable balloon for use in cosmetic surgery to expand an initial longitudinal cavity into a predetermined region of fatty-tissue extending in first and second opposite directions transverse to the initial cavity to form a final cavity, the system comprising:

an elongate means having spaced proximal and distal ends and adapted at its proximal end to receive an inflation fluid and having at least one port at a location distal to the proximal end for supplying inflation fluid to the inflatable balloon;

a balloon comprising two like panels of pliant but essentially non-stretch material conforming generally to a predetermined region within a fatty-tissue and secured to the elongate means along a longitudinal alignment distal with respect to the proximal end and otherwise peripherally secured to each other, such that the port is in communication with the balloon, and such that the balloon conforms to the predetermined region as fractional areas of the predetermined region, wherein the fractional areas extend in opposite directions transverse to the elongated means;

the balloon being capable of initially being in an uninflated state wherein the balloon is precoiled and operatively connected to the elongate means; and whereby, upon insertion of the system into the initial cavity, the balloon is capable of conforming to an inflatable state such that when the balloon is inflated, the balloon deploys in a pattern that permits the balloon to remain in the initial plane within a fatty-tissue, wherein in the inflated state, the balloon is capable of expanding within a fatty-tissue to an inflated state and throughout the fractional areas within a fatty-tissue to form the final cavity within a fatty-tissue which collectively conform substantially to the predetermined region.

3. A system including an inflatable balloon for use in cosmetic surgery to expand an initial longitudinal cavity into a predetermined region of fatty-tissue extending transverse to the initial cavity to form a final cavity, the system comprising:

an elongate cannula having spaced proximal and distal ends and adapted at its proximal end to receive an inflation fluid and having at least one port at a location distal to the proximal end adapted to supply inflation fluid to the inflatable balloon;

a balloon comprising two like panels of pliant but essentially non-stretch material conforming generally to a predetermined region within a fatty-tissue and connected to the cannula along a longitudinal alignment distal with respect to the proximal end and otherwise peripherally secured to each other, such that said port is in communication with the balloon;

wherein the length of the balloon connection to the cannula is adapted to be less than the length of a predetermined region of fatty-tissue; and wherein the balloon is capable of defining a local peripheral protuberance which is laterally offset from the cannula, wherein the protuberance is locally tucked between the panels of the balloon such that the balloon is then substantially the the same length as the balloon connection to the cannula; and the balloon having an uninflated state wherein the protuberance is tucked within the two panels in precoiled wrapped condition operatively connected to the cannula, whereby, upon insertion of the system into an initial cavity, the balloon is capable of conforming to an inflated state and the balloon is capable of expanding within a fatty-tissue and throughout an area within a fatty-tissue which is laterally offset with respect to the cannula to form a final cavity and which also conforms substantially to the predetermined region upon fluid-driven expulsion of the tucked region to define the local peripheral protuberance.

4. A system for use in surgery requiring tissue dissection, elevation or repositioning for expanding an initial cavity formed within a predetermined region of fatty-tissue extending transverse to the initial cavity into a larger final cavity, the system comprising:

means for positioning an inflatable means in an initial cavity, the positioning means having spaced proximal and distal ends and having at least one port for supplying inflation fluid to an inflatable means, the inflatable means being adapted to receive an inflation fluid; and the inflatable means capable of being in an uninflatable state, the inflatable means comprising:

two like panels of pliant but essentially non-stretch material conforming generally to a predetermined region of fatty-tissue operatively connected to the positioning means, such that the port is in communication with the inflatable means, the two like panels including asymmetric wings for being folded within the panels, the inflatable means being operatively connected to the positioning means whereby, upon insertion of the system into an initial cavity and upon inflation of the inflatable means, the inflatable means is capable of expanding within a fatty tissue and throughout an area within a fatty-tissue which is laterally offset with respect to the initial cavity and the asymmetric wings are capable of deploying from the folded position within the panels to form a final cavity which conforms substantially to a predetermined region.

5. A system including an inflatable balloon for use in surgery requiring tissue dissection, elevation or repositioning for expanding an initial longitudinal cavity by dissection into a predetermined region of fatty-tissue extending in first and second opposite directions transverse to the initial cavity to form a final cavity, the system comprising:

means for positioning an inflatable means in an initial cavity, the positioning means having spaced proximal and distal ends and having at least one port for supplying inflation fluid to an inflatable balloon, the inflatable balloon being adapted to receive an inflation fluid; and a balloon capable of being in an uninflated state, the balloon comprising:

two like panels of pliant but essentially non-stretch material conforming generally to a predetermined region of fatty-tissue operatively connected to the positioning means, such that the port is in communication with the balloon, the two like panels including asymmetric wings, folded within the panels, being capable of extending the dissection laterally of and behind the point of insertion; and the balloon being operatively connected to the positioning means, whereby, upon insertion of the system into the initial cavity and upon inflation, the balloon is capable of expanding within a fatty-tissue and throughout an area which is laterally offset with respect to an initial cavity and the asymmetric wings are capable of deploying from the folded position within the panels and throughout the fractional areas to form a final cavity which collectively conform substantially to a predetermined region.

6. A system including an inflatable balloon for use in surgery requiring tissue dissection, elevation or repositioning to expand an initial longitudinal cavity into a predetermined region of fatty-tissue extending transverse to the initial cavity to form a final cavity, the system comprising:

positioning means having spaced proximal and distal ends and being adapted for receiving an inflation fluid and having at least one port for supplying inflation fluid to an inflatable balloon;

an inflatable balloon comprising two like panels of pliant but essentially non-stretch material conforming generally to a predetermined region of fatty-tissue and operatively connected to the positioning means such that the port is in communication with the inflatable balloon;

a predetermined region of fatty-tissue being of greater longitudinal extent than the longitudinal extent of the inflatable balloon connection to the positioning means, thereby defining a local peripheral protuberance of the inflatable balloon at lateral offset from the positioning means, the protuberance being tucked between the panels to the extent that the tucked balloon is of substantially the longitudinal extent of the balloon connection to the positioning means; and the balloon being capable of initially being in an uninflated state and in tucked condition and in a precoiled wrapped condition whereby, upon insertion of the system from a point of insertion and along an axis of insertion into an initial cavity and upon inflation of the balloon, the balloon is capable of expanding within the fatty-tissue and throughout an area which is laterally offset with respect to the positioning means to form a final cavity conforming substantially to a predetermined region of fatty-tissue upon fluid-driven expulsion of the tucked region to define the local peripheral protuberance, the predetermined region of fatty-tissue including a region that extends back from the point of insertion and across the axis of insertion.

* * * * *